US012596124B2

(12) United States Patent
Yamamoto et al.

(10) Patent No.: US 12,596,124 B2
(45) Date of Patent: *Apr. 7, 2026

(54) MULTI-SPECTRAL MICROPARTICLE-FLUORESCENCE PHOTON CYTOMETRY

(71) Applicant: MIFTEK CORPORATION, West Lafayette, IN (US)

(72) Inventors: Masanobu Yamamoto, West Lafayette, IN (US); J. Paul Robinson, West Lafayette, IN (US)

(73) Assignee: Miftek Corporation, West Lafayette, IN (US)

( * ) Notice: Subject to any disclaimer, the term of this patent is extended or adjusted under 35 U.S.C. 154(b) by 38 days.

This patent is subject to a terminal disclaimer.

(21) Appl. No.: 18/519,724

(22) Filed: Nov. 27, 2023

(65) Prior Publication Data

US 2024/0125790 A1 Apr. 18, 2024

Related U.S. Application Data

(60) Division of application No. 16/840,220, filed on Apr. 3, 2020, now Pat. No. 11,835,525, which is a
(Continued)

(51) Int. Cl.
| | |
|---|---|
| *G01N 15/1434* | (2024.01) |
| *B01L 3/00* | (2006.01) |
| *G01N 15/14* | (2006.01) |
| *G01N 15/1429* | (2024.01) |
| *G01N 33/49* | (2006.01) |

(Continued)

(52) U.S. Cl.
CPC .............. *G01N 33/582* (2013.01); *B01L 3/00* (2013.01); *G01N 15/1427* (2013.01); *G01N 15/1429* (2013.01); *G01N 15/1434* (2013.01); *G01N 33/4915* (2013.01); *G01N 35/00069* (2013.01); *G01N 15/1456* (2013.01); *G01N 15/1459* (2013.01); *G01N 15/1484* (2013.01);
(Continued)

(58) Field of Classification Search
CPC .............. G01N 33/582; G01N 33/4915; G01N 15/1427; G01N 15/1429; G01N 15/1434; G01N 35/00069
See application file for complete search history.

(56) References Cited

U.S. PATENT DOCUMENTS 7,280,204 B2 * 10/2007 Robinson ........... G01N 15/1459
356/306
11,835,525 B2 * 12/2023 Yamamoto ......... G01N 15/1434
(Continued)

*Primary Examiner* — Gailene Gabel
(74) *Attorney, Agent, or Firm* — Piroozi-IP, LLC

(57) ABSTRACT

A measurement system is disclosed which includes a spot-traversal system for causing relative motion between a sample and an irradiation spot in a first direction, wherein the sample includes one or more fluorescent markers having respective fluorescence wavelengths, a gating system configured to provide a gating signal based at least in part on resultant light substantially at a wavelength of the irradiation spot, and an optical detection system configured to detect fluorescent light from at least some of the fluorescent markers irradiated by the irradiation spot, and provide detection signal(s) representing the fluorescent light detected concurrently with a gate-open condition of the gating signal.

8 Claims, 22 Drawing Sheets

Related U.S. Application Data continuation of application No. 15/250,136, filed on Aug. 29, 2016, now Pat. No. 10,613,096.

(60) Provisional application No. 62/211,452, filed on Aug. 28, 2015.

(51) Int. Cl.
    *G01N 33/58*     (2006.01)
    *G01N 35/00*     (2006.01)
    *G01N 21/64*     (2006.01)

(52) U.S. Cl.
    CPC . *G01N 21/645* (2013.01); *G01N 2035/00881* (2013.01); *G01N 2201/1045* (2013.01)

(56) References Cited

U.S. PATENT DOCUMENTS

| | | | |
|---|---|---|---|
| 2002/0176342 A1* | 11/2002 | Worthington | G01N 15/1433 |
| 2012/0156714 A1* | 6/2012 | O'Brien | G01N 21/6428 |
| | | | 435/29 |
| 2015/0083903 A1* | 3/2015 | Gilmore | G01N 21/33 |
| | | | 250/214 R |

* cited by examiner

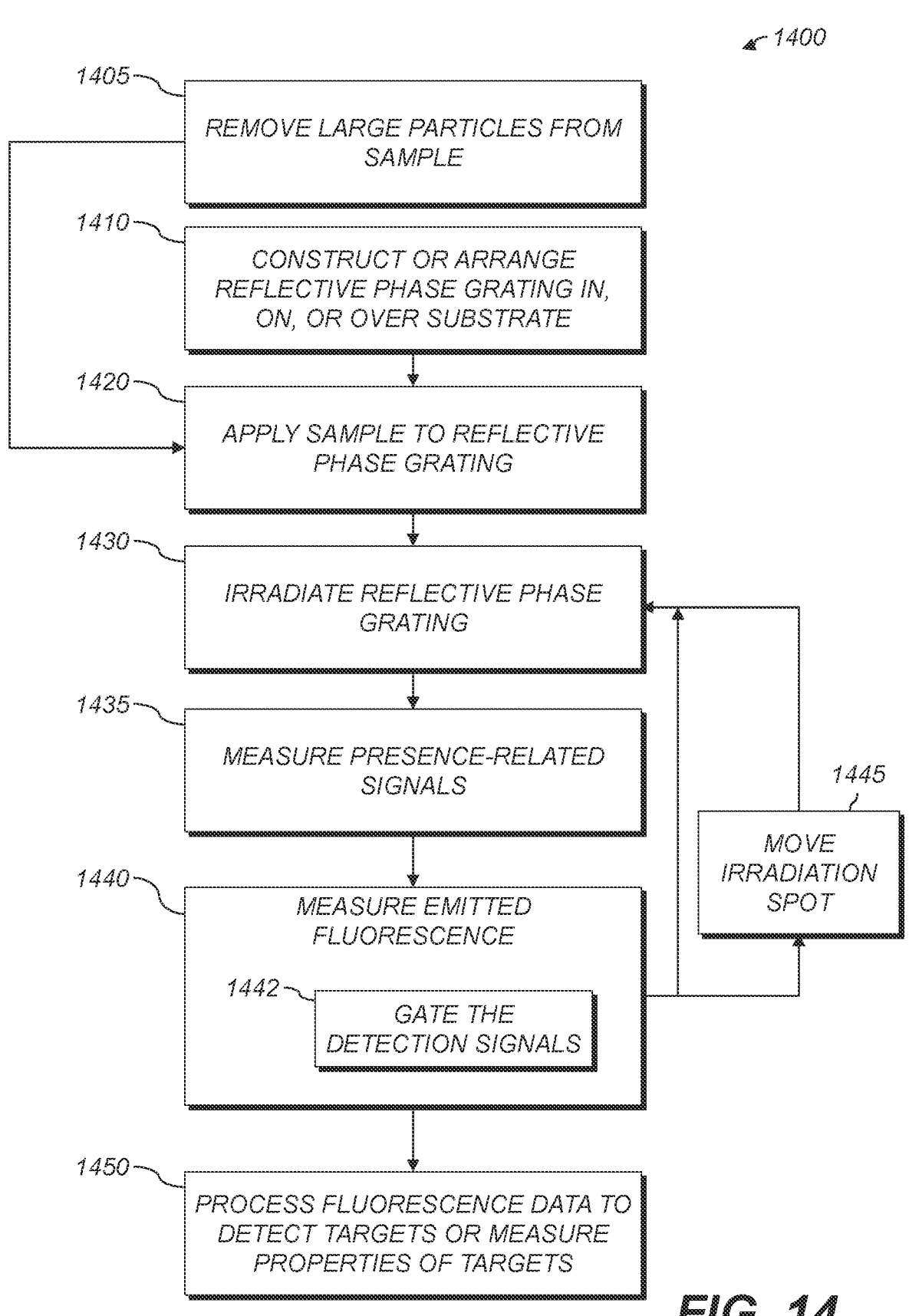

*1400*

1405 — REMOVE LARGE PARTICLES FROM SAMPLE

1410 — CONSTRUCT OR ARRANGE REFLECTIVE PHASE GRATING IN, ON, OR OVER SUBSTRATE

1420 — APPLY SAMPLE TO REFLECTIVE PHASE GRATING

1430 — IRRADIATE REFLECTIVE PHASE GRATING

1435 — MEASURE PRESENCE-RELATED SIGNALS

1440 — MEASURE EMITTED FLUORESCENCE

1442 — GATE THE DETECTION SIGNALS

1445 — MOVE IRRADIATION SPOT

1450 — PROCESS FLUORESCENCE DATA TO DETECT TARGETS OR MEASURE PROPERTIES OF TARGETS

*FIG. 14*

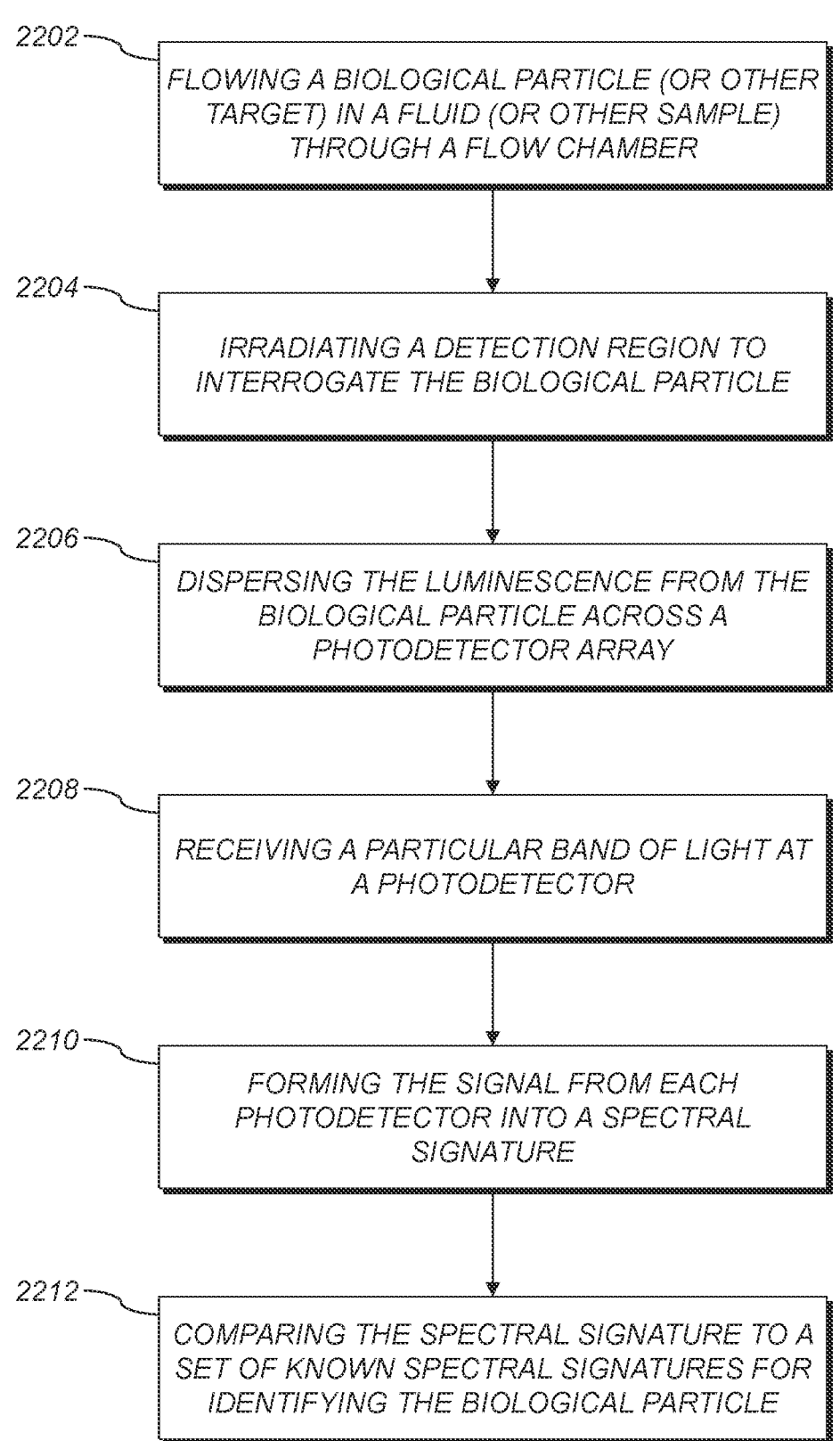

2202 — FLOWING A BIOLOGICAL PARTICLE (OR OTHER TARGET) IN A FLUID (OR OTHER SAMPLE) THROUGH A FLOW CHAMBER

2204 — IRRADIATING A DETECTION REGION TO INTERROGATE THE BIOLOGICAL PARTICLE

2206 — DISPERSING THE LUMINESCENCE FROM THE BIOLOGICAL PARTICLE ACROSS A PHOTODETECTOR ARRAY

2208 — RECEIVING A PARTICULAR BAND OF LIGHT AT A PHOTODETECTOR

2210 — FORMING THE SIGNAL FROM EACH PHOTODETECTOR INTO A SPECTRAL SIGNATURE

2212 — COMPARING THE SPECTRAL SIGNATURE TO A SET OF KNOWN SPECTRAL SIGNATURES FOR IDENTIFYING THE BIOLOGICAL PARTICLE

*FIG. 22*

SPHERICAL MIRROR

IMAGING PLANE

LIGHT SOURCE

TOROIDAL MIRROR

IMAGING PLANE

LIGHT SOURCE

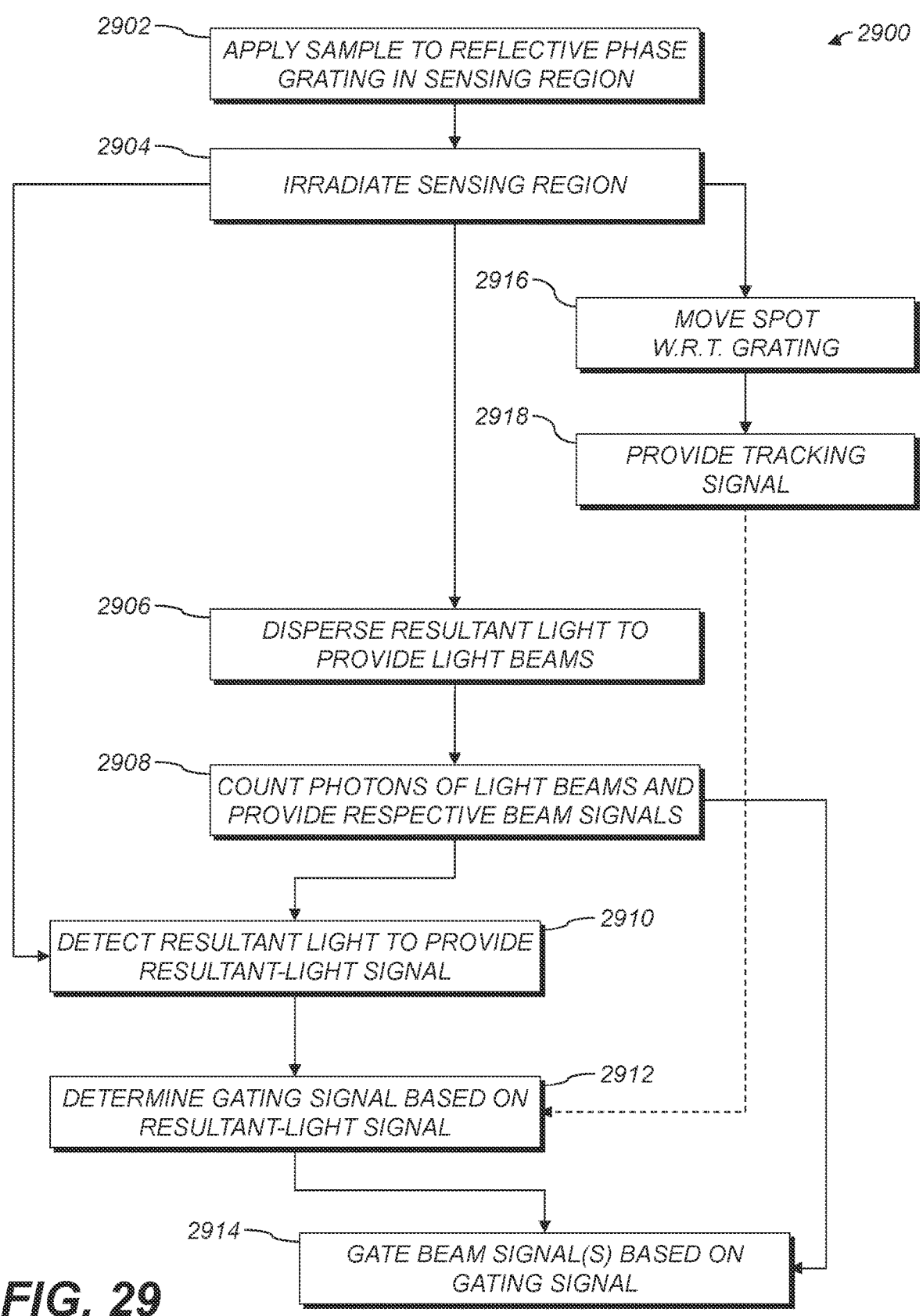

2902 — APPLY SAMPLE TO REFLECTIVE PHASE GRATING IN SENSING REGION

2900

2904 — IRRADIATE SENSING REGION

2916 — MOVE SPOT W.R.T. GRATING

2918 — PROVIDE TRACKING SIGNAL

2906 — DISPERSE RESULTANT LIGHT TO PROVIDE LIGHT BEAMS

2908 — COUNT PHOTONS OF LIGHT BEAMS AND PROVIDE RESPECTIVE BEAM SIGNALS

2910 — DETECT RESULTANT LIGHT TO PROVIDE RESULTANT-LIGHT SIGNAL

2912 — DETERMINE GATING SIGNAL BASED ON RESULTANT-LIGHT SIGNAL

2914 — GATE BEAM SIGNAL(S) BASED ON GATING SIGNAL

FIG. 29

MULTI-SPECTRAL MICROPARTICLE-FLUORESCENCE PHOTON CYTOMETRY

CROSS-REFERENCE TO RELATED APPLICATIONS

This application is a continuation of and claims priority to U.S. patent application Ser. No. 16/840,220 filed on Apr. 3, 2020 which is a continuation of and claims priority to U.S. patent application Ser. No. 15/250,136, filed on Aug. 29, 2016, which is a nonprovisional of and claims priority to U.S. Pat. Appl. Ser. No. 62/211,452, filed Aug. 28, 2015, each of which is incorporated herein by reference in its entirety.

BRIEF DESCRIPTION OF THE DRAWINGS

Objects, features, and advantages of various aspects will become apparent when taken in conjunction with the following description and drawings. Identical reference numerals have been used, where possible, to designate identical features that are common to the figures.

FIG. 14 is a flowchart according to various aspects.

FIG. 22 is a flowchart according to various aspects.

FIG. 29 is a flowchart according to various aspects.

Figure 1:
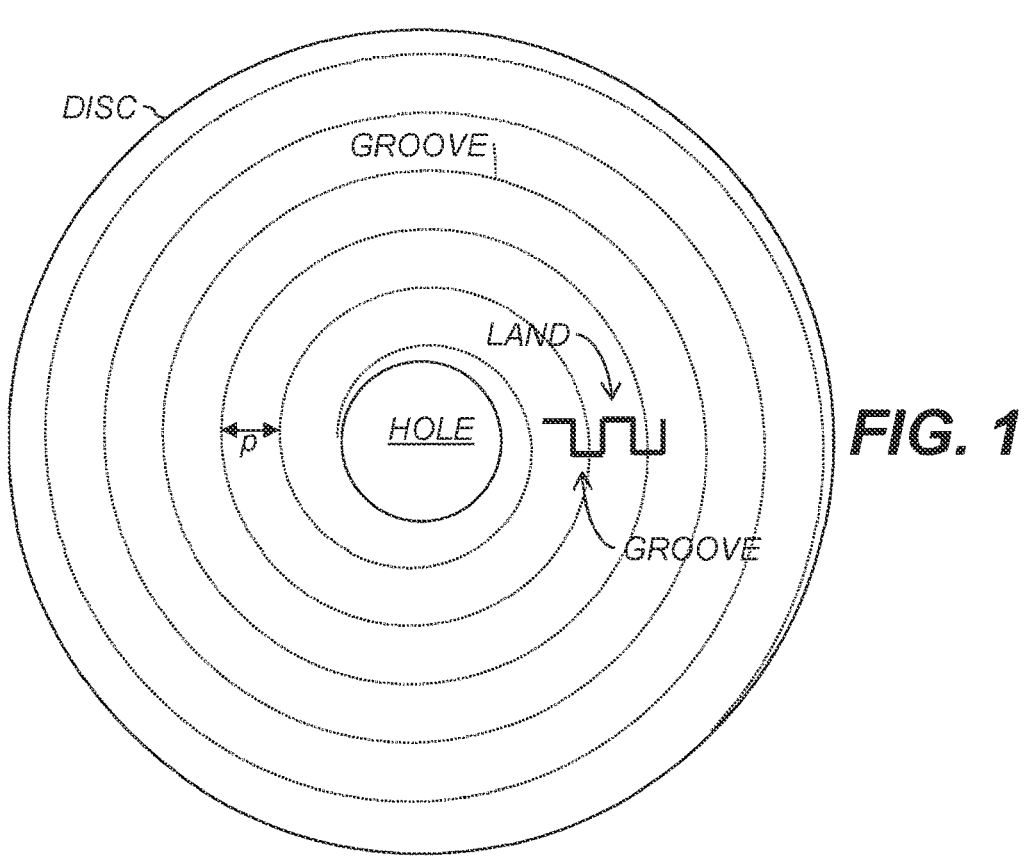
FIG. 1 shows example spiral tracks on discs.

The attached drawings are for purposes of illustration and are not necessarily to scale.

DETAILED DESCRIPTION

Overview

Throughout this description, some aspects are described in terms that would ordinarily be implemented as software programs. Those skilled in the art will readily recognize that the equivalent of such software can also be constructed in hardware, firmware, or micro-code. Because data-manipulation algorithms and systems are well known, the present description is directed in particular to algorithms and systems forming part of, or cooperating more directly with, systems and methods described herein. Other aspects of such algorithms and systems, and hardware or software for producing and otherwise processing signals or data involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Various aspects relate to a quantitative microvesicle (MV) measurement platform. Some examples use a focused scanning laser spot on a grating, e.g., a reflective grating. Some examples provide single photon spectroscopy or single photon cytometry. Microvesicles can be intracellular or extracellular. Extracellular vesicles (EVs) can include, e.g., substantially spherical EVs having diameters between 30 nm and 1000 nm; tubular or other substantially elongated EVs between 1 µm and 5 µm in size; or EVs between 4 nm and 500 nm in size. Example targets can include high-density lipoprotein (HDL) EVs of ~10 nm in size or low-density lipoprotein (LDL) EVs of ~22 nm in size. Other targets can include large fragments up to about 8 µm in size.

In some examples, microvesicles can be present in human blood plasma in concentrations from $10^4$-$10^{12}$ per mL. In some examples, over 80% of vesicles in a sample can have diameters less than 100 nm. Vesicles can have an index of refraction n, e.g., of about 1.40, compared to silica at n≈1.45 and polystyrene at n≈1.61. In some prior flow-cytometry schemes, microvesicles such as liposomes having diameters≈100 nm can be difficult to distinguish from threshold noise in the system.

In the fields related to life sciences such as genetics, immunology, molecular biology, and environmental science, optical techniques are widely used to analyze microparticulate targets such as living cells, yeast, and bacteria. For example, particles or cells from 500 nm up to 50 micron can generally be measured in flow cytometry. The terms "optical" and "light" are not limited to the visible range of, e.g., 400 nm-700 nm unless otherwise expressly specified. In some examples, a label made of a fluorescent substance is attached to the surface of a target cell to be analyzed. As used herein, a "fluorescent marker" is a substance capable of fluorescing when exposed to radiant energy of a corresponding wavelength. Next, laser light is radiated towards a predetermined position to irradiate the cell. Then, forward-scattered light and side-scattered light, which are generated due to the size and structure of each cell, and fluorescence, which is generated by excitation due to the light irradiation, are observed. In the case of observing fluorescence from a cell, a configuration for spectral analysis of the fluorescence condensed in a direction other than an irradiation path of excitation light is widely used to avoid adverse effects of transmitted or scattered excitation light. Fluorescent substances to be attached or combined for each type of cells are known. Accordingly, the wavelength and intensity of the fluorescence are observed and the intensity component to be superimposed is compensated to thereby identify the type of each cell.

There is a need for detecting and measuring sub-structures within cells or produced by cells. For example, cells can produce or receive "vesicles" or "microvesicles," lipid bilayers surrounding proteins, DNA, RNA, mRNA, miRNA, proteins, cytotoxins, waste from metabolic processes, or other components of a cell or substances that can be found within a cell. See, e.g., the above-noted '588 publication. Vesicles can be, e.g., 10 nm-50 nm or 100 nm-1000 nm in mean diameter. Some example vesicles include protein-enriched micro-vesicles. By "protein-enriched micro-vesicle" is meant a fusogenic structure that includes an amount of one or more target proteins in a lipid bilayer envelope. As used herein, the term "fusogenic" refers to the property of the micro-vesicle which provides for the fusion of the membrane of the micro-vesicles to the membrane of the target cell. Fusogenic micro-vesicles are capable of fusion with the lipid bilayer membrane of a target cell to deliver their contents, e.g., the target protein(s), into the cell. As used herein, a "target" can be a microvesicle or other microparticulate structure to be measured. As used herein, a "sample" can be a solid, liquid, or gaseous aggregate of one or more targets. A sample can additionally include non-target substances. For example, a blood sample can include microvesicle targets and plasma; the plasma in this example is a non-target substance.

A quantitative measurement platform, e.g., for microve-sicles, can provide nanoparticle detection on reflective phase grating implemented using a focused scanning laser spot on a reflective phase grating in a microfluidic channel. Various examples of such measurement platforms, systems, and techniques, and simulated and measured data, are described herein. Various example techniques and systems described herein can provide quantitative measurements of particles, e.g., 10 nm-1000 nm in mean diameter. 10 nm is beyond the resolution of many prior optical detection systems. Some prior schemes for high-resolution imaging or particle detection include electron microscopes, Brownian-motion detection of particles in suspension (e.g., NANOSIGHT), and flow cytometry. However, many electron microscopes are unable to observe living cells or cell components such as vesicles since electron microscopy generally involves drying the sample and placing it in a vacuum chamber.

Various aspects herein permit measuring small particles or structures such as vesicles or nanoparticles (individually or collectively, "targets"). Various aspects permit performing such measurements without damaging living cells or microorganisms that are being measured or that area producing the targets being measured. Various aspects can provide quantitative measurements of targets. Various aspects can be used in a clinical environment as a disposable chip or disc (individually or collectively a "lab on chip" or LOC) including sample preparation/processing/target measurement/disposal without the need for free liquid reagents or suspensions. Various aspects use fluorescence to further measure presence or properties of specific targets. Example targets can be substantially equal to, e.g., 100 nm, 70 nm, 50 nm, or 30 nm in diameter. Targets having other diameters can also be measured.

Various aspects include diffraction detection of targets on reflective phase grating structures. Such structures can provide double phase modulation of light traveling through the targets. Various phase gratings provide a microscopic reference scale of sinusoidal signal characteristics.

Illustrative Configurations

FIG. 1 shows an example disk (the spellings "disk" and "disc" are interchangeable herein) with a hole in the center. A spiral track, e.g., a land or groove, is shown dotted and has a fixed pitch p across the surface of the disk. "Lands" include non-recessed or raised areas; "grooves" include recessed or lowered areas. Shown superimposed on the spiral in heavy lines is a cross-section. In the illustrated example, the track follows grooves that are separated by lands of the same widths as the grooves. In this example, the track does not have pits and lands burned along the length of the track as a data-bearing BLU-RAY disc does. In other examples, the track includes some data-bearing areas. In some examples, a single disc carries data-bearing tracks and non-data-bearing tracks. Various examples of reflective phase gratings are discussed and shown herein., e.g., the groove in FIG. 1. However, the orientation(s) of grooves or lands in a reflective phase grating and the orientation(s) of laser spot travel (if any) are not constrained. In some examples, the laser spot moves substantially radially rather than substantially tangentially or substantially along a spiral.

Figure 2:
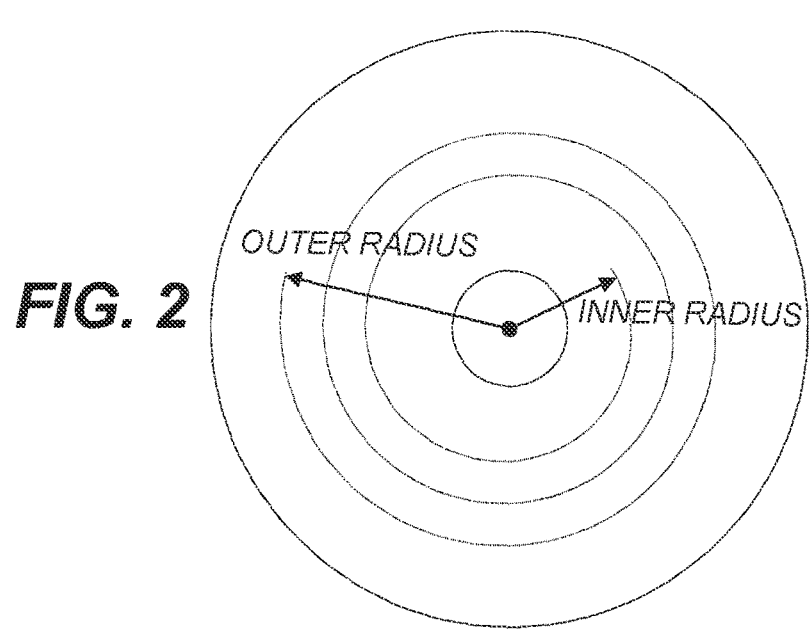
FIG. 2 shows example spiral tracks on discs.

FIG. 2 shows an example disk in which the track does not extend across the full radius of the disk. The track covers a portion of the disc between an inner radius and an outer radius. Multiple tracks can be arranged in different radial zones of the disc. Multiple tracks can be interleaved, e.g., starting from the same radius but 180° around the disc from each other.

Discs can be manufactured having desired numbers of tracks, track pitches, radii, interleaving, groove width, land width, or orientation, using CD, DVD, or BLU-RAY duplication technology. The pitch of the tracks can be selected based on the size of the targets to be detected.

In some examples, the negative pattern of the lands and grooves of the track can be transferred to a stamper, e.g., made of nickel. The stamper can be positioned with respect to an injection mold so that polycarbonate (PC) or another material injection-molded in that mold takes on the desired pattern of lands and grooves. The molded polycarbonate can then be sputter-coated, e.g., with aluminum or silver, e.g., 18 nm thick, to form a reflective surface that can be read by a laser.

In some examples, phase transition mastering (PTM) can be used to manufacture the stamper. PTM involves developing the desired pattern in an inorganic photoresist over a silicon wafer. The wafer can then be etched to prepare the stamper.

In some examples, laser writing such as used in dye-based recordable DVDs can be used to manufacture discs. The desired pattern of grooves can be burned into a dye layer of such a disc using a laser.

Above-described manufacturing techniques for discs can be used to prepare spiral tracks or other shapes or groove or pit patterns in non-circular substrates, e.g., substantially quadrilateral (e.g., rectangular) shapes used for lab-on-chip devices. These devices can be scanned with focused laser light, as described herein. Discs or other lab-on-chip devices can be reusable or disposable.

An optical disc was prepared from a customized master having a track pitch p=500 nm. The master was prepared with phase transition mastering (PTM). A nickel stamper was manufactured and the test disc was injection molded and stamped with the master. Injection molding of transparent polycarbonate was performed, then the polycarbonate was cooled, then aluminum was sputtered over the polycarbonate.

In a constructed example, the disc had a single spiral groove recessed below the majority of the surface of the disc. The groove was arranged between an inner radius of 38 mm and an outer radius of 42 mm. The portions of the disc not bearing a groove are referred to as a "mirror" herein. The groove can be arranged relatively farther from the objective lens during measurement; the land can be relatively closer to the objective lens. The relative widths of the lands and grooves, e.g., shown in the cross-section in FIG. 1, can be substantially equal or can be different. Examples using equal land and groove widths can provide improved push-pull signal SNR.

Figure 15:
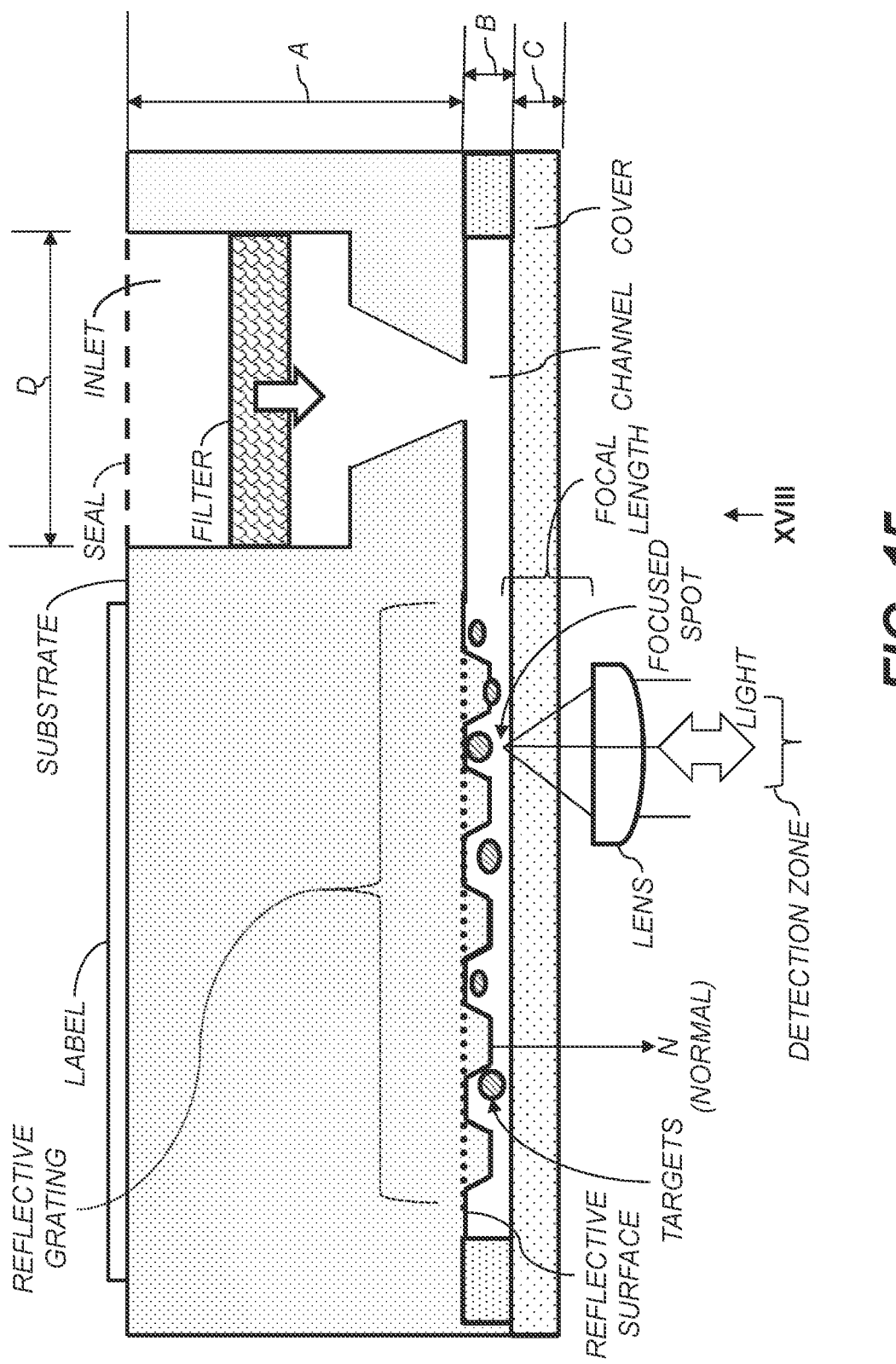
FIG. 15 shows an elevational cross-section of an example lab-on-chip device (LOC) and related components.
Figure 16:
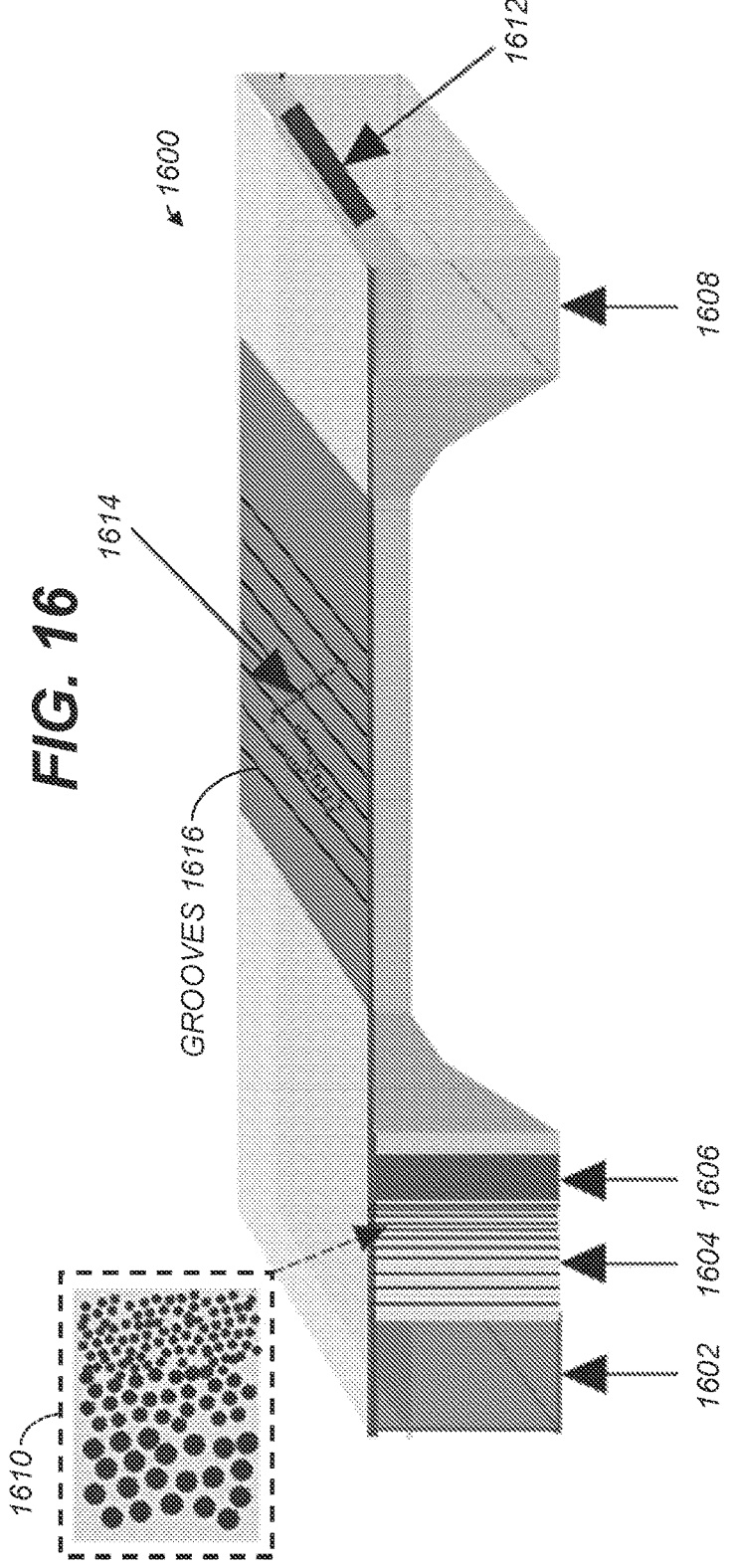
FIG. 16 shows a perspective and partial cross-sections of components of an example LOC, and example groove patterns.

One or more portions of a disc or other LOC can have respective groove patterns (e.g., spiral, straight, concentric circles, or other curves). Different portions can have different patterns or the same pattern, in any combination. In an example, at least two portions of a disc-shaped LOC have spiral groove patterns with different pitch values (p). This can permit effectively detecting targets in different size ranges. A LOC (disc or otherwise) can have one or more sample inlets, vacuum outlets (e.g., ports or channels to which vacuum can be applied to move sample), or one or more detection zones. Example LOCs according to various aspects are shown in FIGS. 3, 15, and 16.

Figure 3:
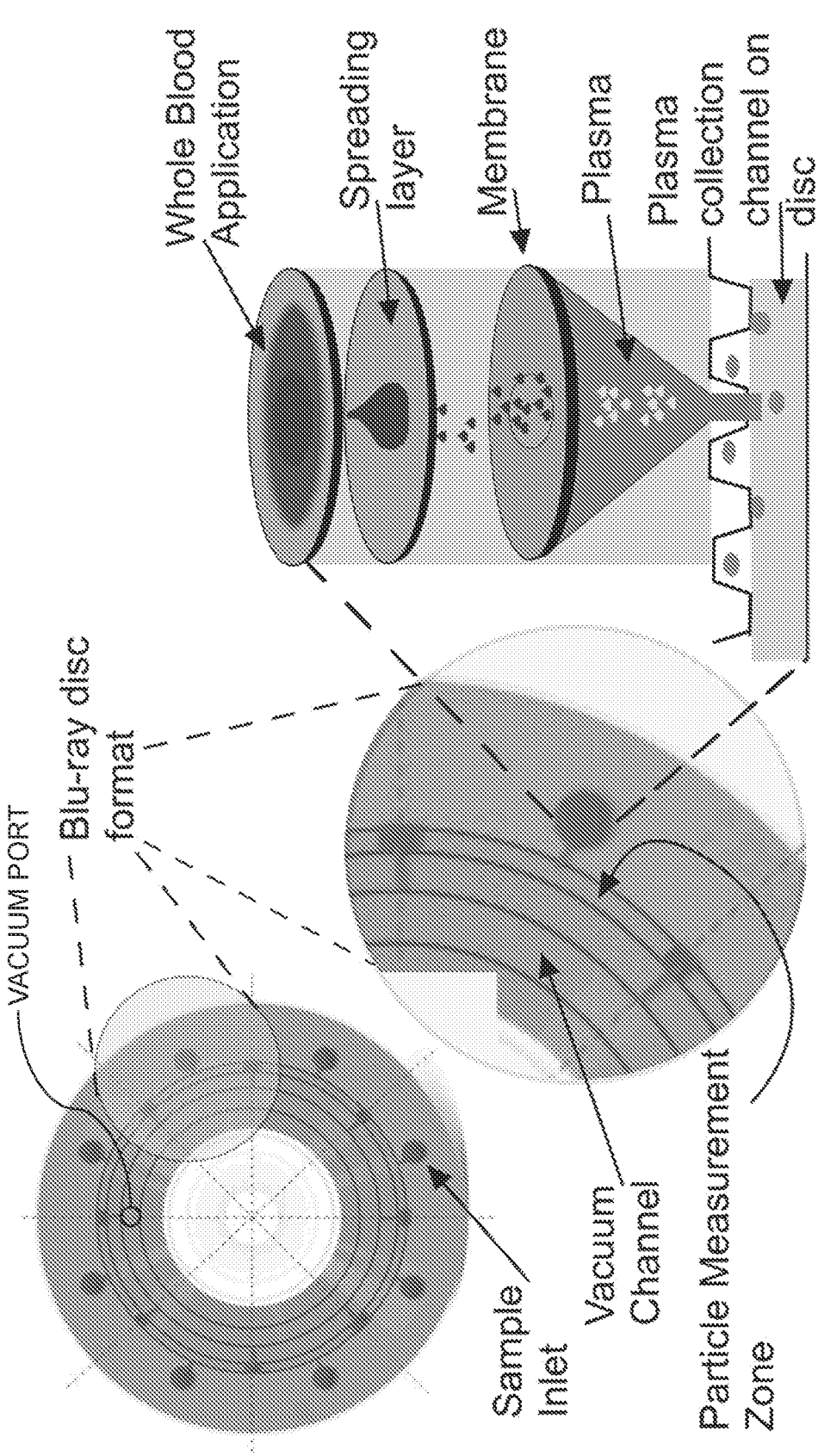
FIG. 3 shows components of an example lab-on-disc configured, e.g., for analysis of blood samples.

FIG. 3 shows an example disc and filter system configured for separation of plasma containing microparticles, e.g., microvesicles. The illustrated filter system can alternatively be used with other configurations of lab-on-chip or reflective grating, e.g., glass slides. Samples can flow through channels in the lab-on-disc or lab-on-chip, e.g., due to vacuum pressure via the illustrated vacuum channel, due to capillary force, or due to other forces. Vacuum pressure can be applied to the vacuum channel through at least one vacuum port (for brevity, only one is shown).

Any number of sample inlets, vacuum channels or ports, or measurement zones (or regions, and likewise throughout) can be used. Vacuum can also or alternatively be applied via vacuum ports. Samples or vacuum can be applied before or during relative motion of the laser spot and disk. Capillary channels, e.g., micropillar channels, or other features can be used to draw sample into the measurement zones.

Micropillars, inlets, channels, ports, and other features shown can be formed using stampers in an injection mold, e.g., as for the reflective phase grating, or can be formed using etching, machining, or other techniques. Multiple layers of a disc or other LOC can be prepared separately and affixed, or layers can be built up or formed together or one after another, in any combination.

Any number of the, e.g., 8 samples can be applied substantially simultaneously, or at different times. Any number of samples can be measured in a single rotation of the disc or other single laser pass across the reflective phase grating, or in multiple passes, in any combination.

Figure 4:
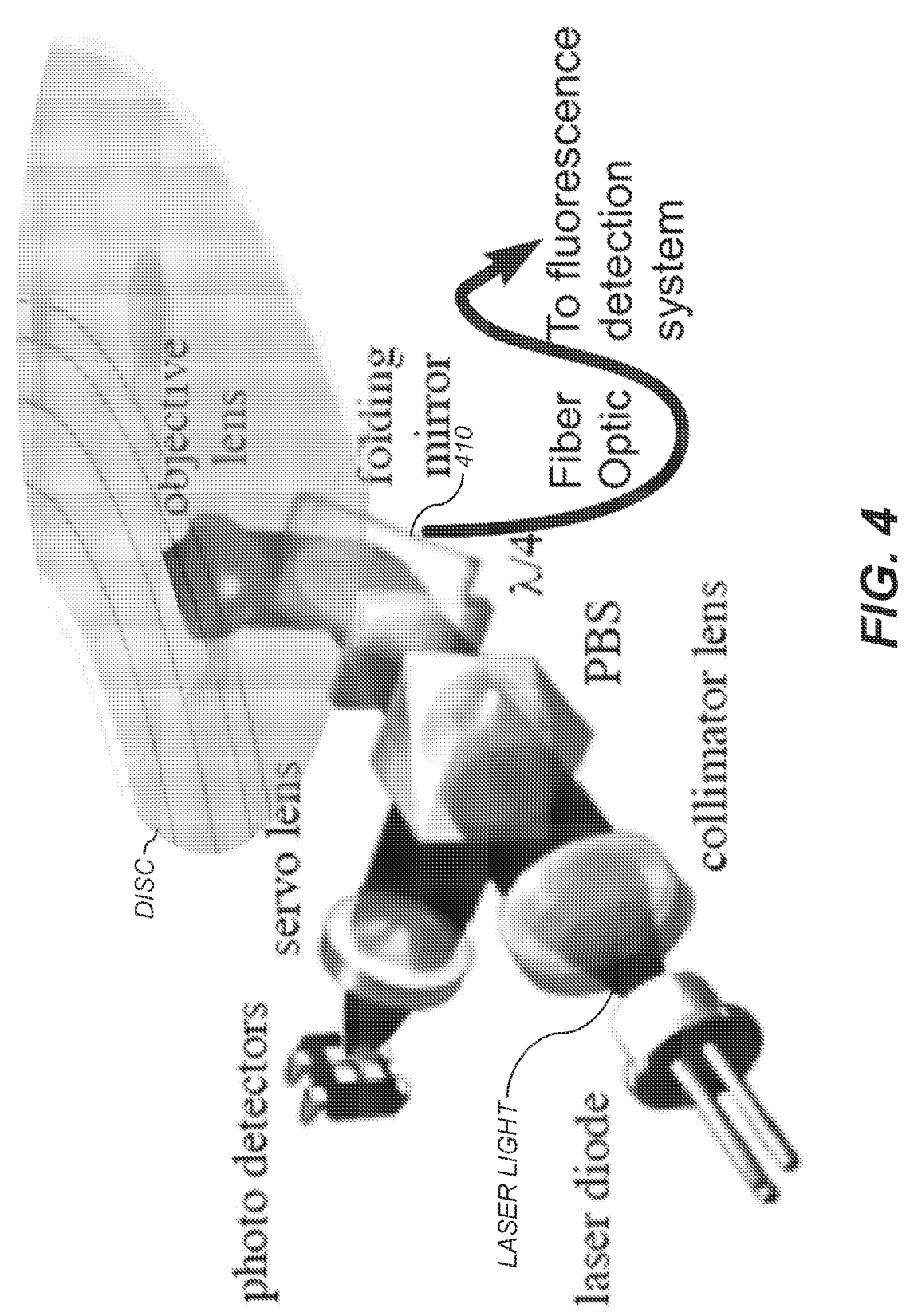
FIG. 4 shows components of an example optical detection assembly useful for detecting or measuring samples, e.g., microvesicles.

FIG. 4 shows example optical apparatus, e.g., including a BLU-RAY optical pick up. In the illustrated example, optical radiation from a laser diode strikes a disc. The laser light, or other light radiated onto or into the disc or other reflective phase grating, is referred to herein as "incident light." In some examples, the incident light can pass into or through a flow chamber, e.g., to irradiate samples or targets in the flow chamber.

Light reflected or refracted from the disc, or light emitted from samples, targets, dyes such as fluorescent dyes, or other substances in or over the disc, is referred to herein as "resultant light." In flow-chamber configurations, resultant light can include light transmitted through the flow chamber. Resultant light can include forward-scattered (FS) light and side-scattered (SS) light. FS and SS can have substantially the same wavelength as the light source does. Resultant light can also include fluorescent light, e.g., emitted by substances in or over the irradiated surface (or within the flow chamber) such as labeled antibodies. Resultant light can be, e.g., substantially directional (e.g., transmitted light of the laser light or substantially omnidirectional (e.g., fluorescence).

It is not required that all of the laser light be incident on any particular target (e.g., a microvesicle). For example, useful information can be gathered while scanning the irradiation spot over the membrane of a microvesicle, even if some of the irradiation spot is not striking the microvesicle.

In various aspects, light provided by a source other than a laser is used instead of or in addition to the laser light. The light source can be any source that can be focused to produce an irradiation spot, e.g., a diffraction-limited spot, a spot having a FWHM<2 µm, or a spot smaller than the target to be irradiated. Example sources can include, e.g., a lamp positioned at the focus off parabolic reflector, or a light-emitting diode (LED) focused through a lens.

In an example, transmitted light or forward-scattered light can be coherent light that is affected by scattering, refraction, absorption, rotation of the plane of polarization, or other effects on the light due to the irradiation of the laser light onto the targets. In an example, the fluorescence or side-scattered light can be incoherent light. Coherent side-scatter and back-scatter light can also be detected.

In some configurations, targets are detected using outputs from the photodetectors. In the illustrated example, at least some resultant light passes back towards folding mirror 410. In some configurations, the coating of the folding mirror 410 is selected to transmit some light from fluorescent dyes in or bonded to targets. Such light can be collected by the fiber optic cable or other collection optics. In some configurations, the coating of the folding mirror 410 is selected to reflect some light having a wavelength similar to that of the incident light. The illustrated polarizing beamsplitter, or another beamsplitter, can be used to direct the resultant light having the wavelength similar to that of the incident light to, e.g., split photodetectors. In some examples, the linear velocity of a target over the objective lens is ~1 m/s. In some examples not shown, a flow cell is used that carries targets at, e.g., ~1 m/s.

In some examples using incident light at ~405 nm from the laser diode, the folding mirror 410 is ~100% reflective at 405 nm. In some examples, in order to get fluorescence (Fl) light through mirror 410, a coating with R405≈100% (reflectance at 405 nm) and T>405 nm≈100% (transmission at wavelengths longer than 405 nm) is applied to mirror 410.

Figure 5:
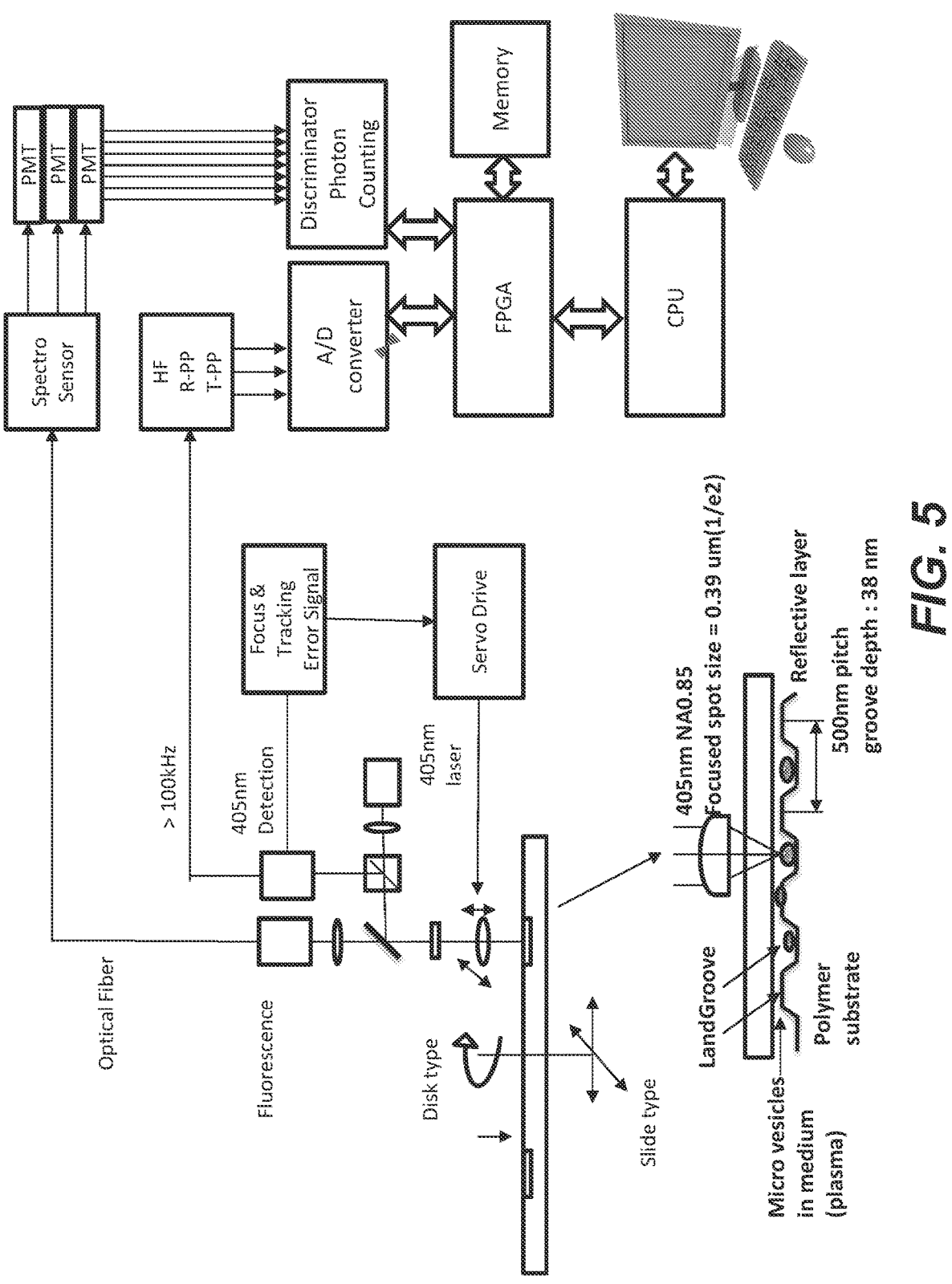
FIG. 5 shows a block diagram of an example measurement system.

FIG. 5 shows an Example Quantitative Microvesicle Measurement Platform. The illustrated example includes a focused scanning laser spot on reflective grating and single photon spectroscopy. However, the illustrated land/groove (L/G) structure is not used in some examples. Conventional flow cell and optics illuminate 800~1000 microvesicles at the same time. This can make it difficult to distinguish individual particles and fluorescence thereof. Some prior schemes dilute samples ~1000×, but this can reduce microvesicle concentration to 1/100 μm³, making it difficult to measure the microvesicles.

Some examples (not shown) use a flow cell and a small spot to illuminate one particle at a time in the spot. For example, a 1 μm narrow-gap flow cell can provide a microvesicle concentration of ~10 μm×10 μm area per particle. A 0.4-μm spot can be used. These parameters can provide individual measurement of one particle in a spot at a time.

Figure 6:
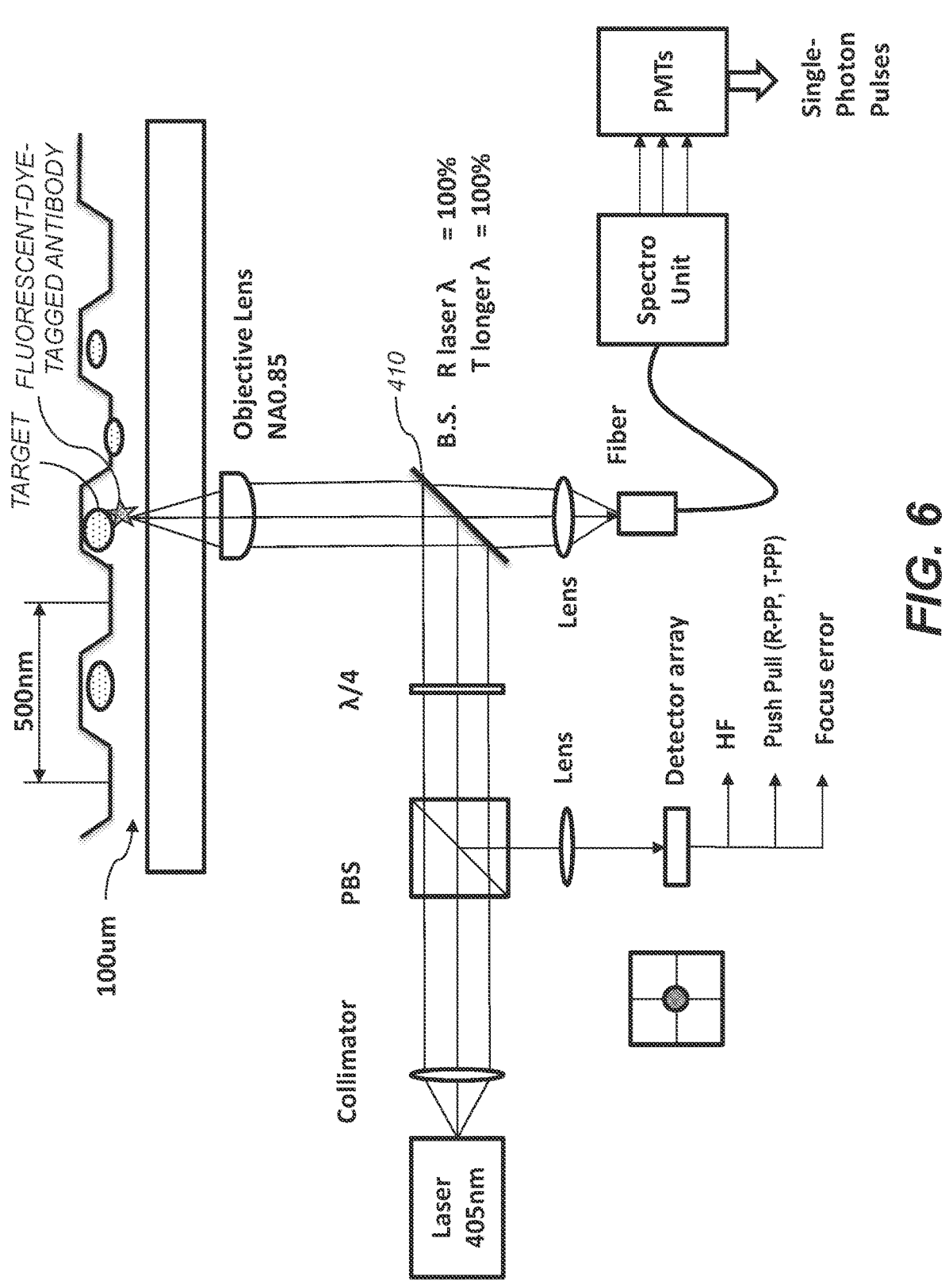
FIG. 6 shows components of an example measurement system, including optical detection components.

FIG. 6 shows example detection optics, e.g., for microvesicles. In the illustrated example, a laser (e.g., λ=40.5 nm) illuminates a reflective grating (e.g., a lab-on-disc) through an objective lens. As shown, a target (e.g., a microvesicle or other microparticle) is arranged over the reflective grating. An antibody is bound to the target. In this example, the antibody is tagged with a fluorescent dye. When the illumination strikes the dye, the die fluoresces. Additionally, the reflective grating and the target interact to modulate, scatter, reflect, or refract some of the incident light.

Figure 17:
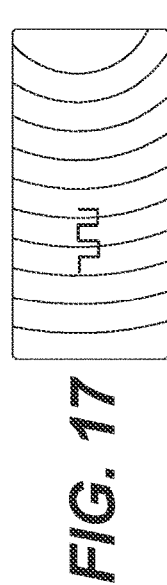
FIG. 17 shows an example plan view of grooves on an example LOC.
Figure 18:
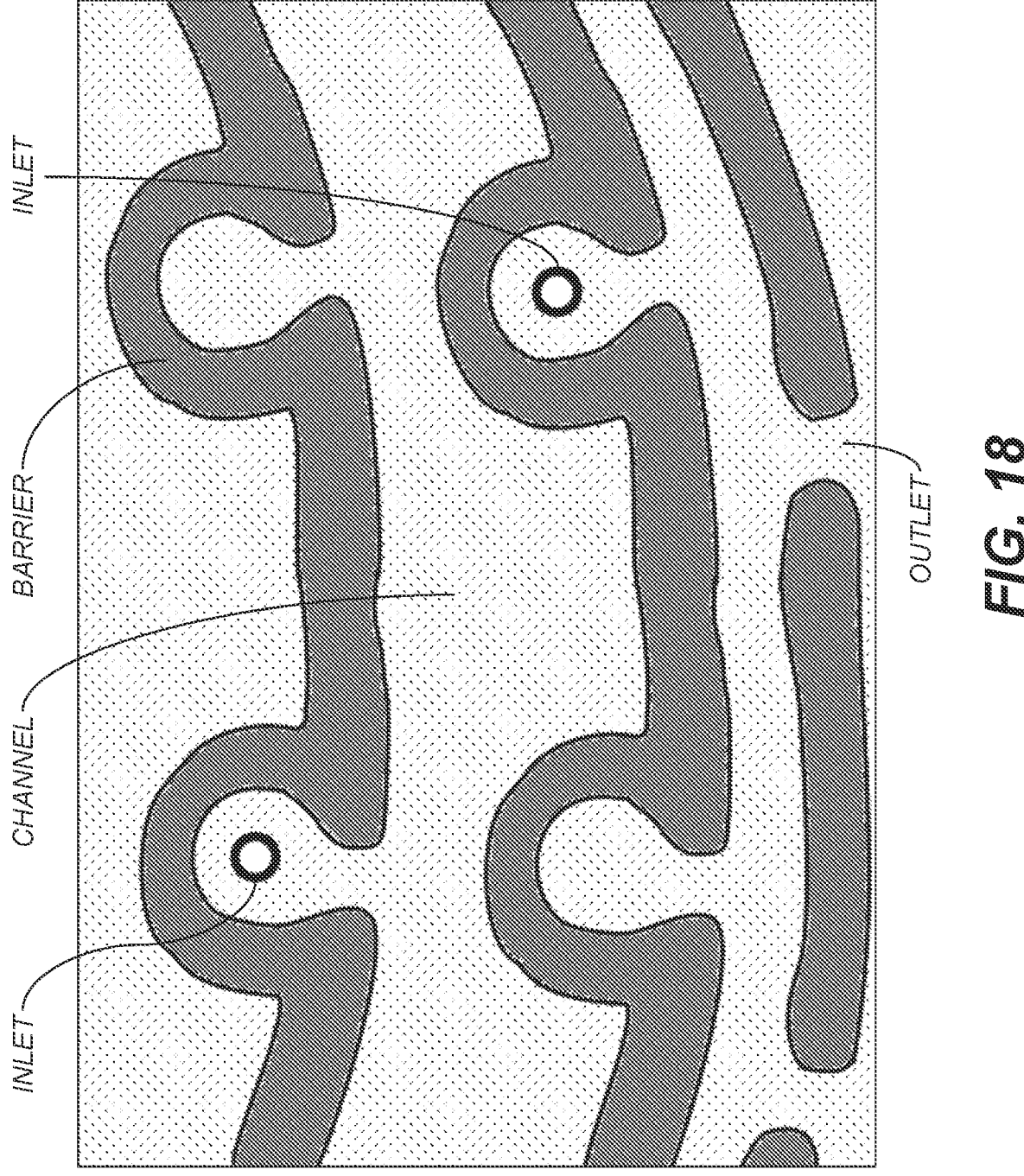
FIG. 18 shows an example plan view of fluid-handling components on an example LOC, e.g., a lab-on-disc.
Figure 19:
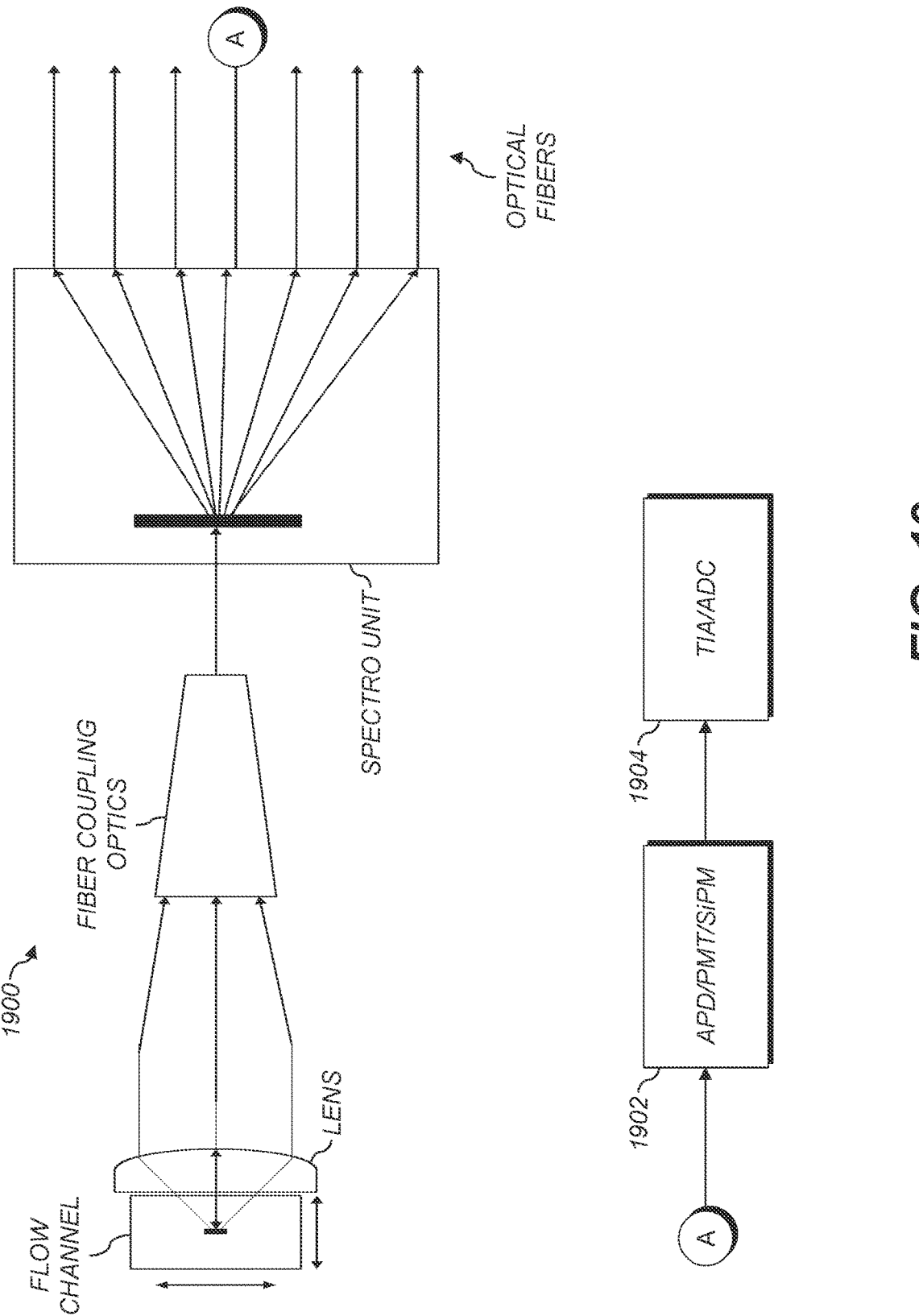
FIG. 19 shows components of an example optical system for multi-channel detection.
Figure 21:
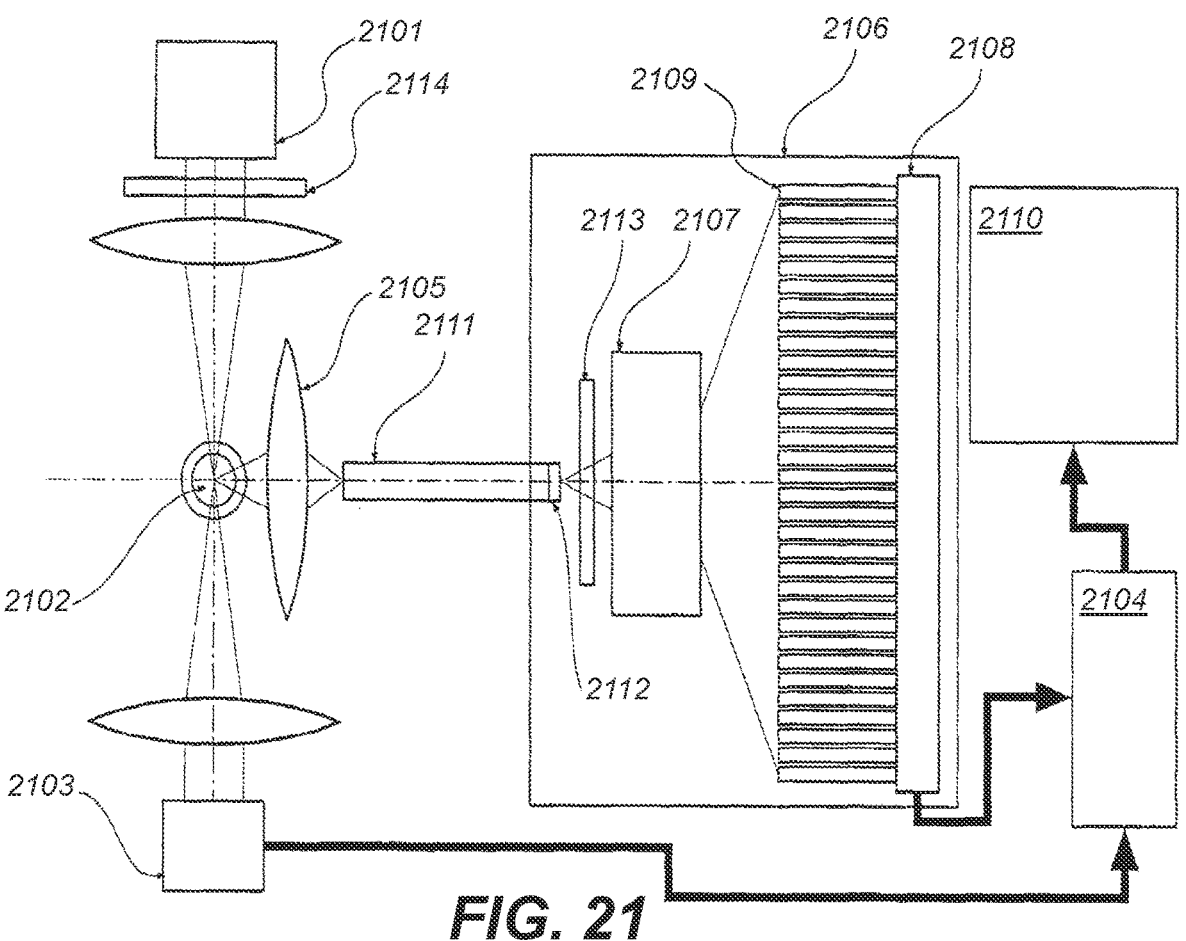
FIG. 21 shows components of an example optical system for multi-channel detection.

In the illustrated example, reflected light from the grating at the incident wavelength is passed through a polarizing or other beamsplitter to a detector array to produce high-frequency (HF), radial push-pull (R-PP), tangential push-pull (T-PP), or focus error signals. Light not at the incident wavelength, e.g., emitted by fluorescent dyes on antibodies bound to targets in the sample, passes through mirror 410 and is collected by a lens and coupled into an optical fiber, e.g., a tapered quartz fiber or other tapered fiber or quartz fiber. The fiber carries the light to a disperser, e.g., a prism, polychromator, or another spectral discriminator or disperser ("spectro unit"). A spectral discriminator can, e.g., separate light at various wavelengths or absorb light at wavelengths not of interest. Light at various wavelengths can be provided, in sequence or in parallel, to one or more photomultiplier tubes (PMTs) or other optical detectors. Example detectors and example spectral discriminators are shown in FIGS. 17-19. Examples can include dichroic mirrors/filters, gratings, prism spectro units, or other discriminators that separate photons based on wavelength or photon energy. Example spectral discriminators and sensors that can be used in various examples are described in U.S. Pat. No. 7,280,204, incorporated herein by reference. An example spectral discriminator useful with various examples is shown in FIG. 21. Acts useful with various examples can include those described with reference to FIG. 22.

In order to collect the Fl light to the fiber, a collimator lens can be used, e.g., a collimating aspherical lens similar to that used to collimate laser light. In some examples, the 405 nm irradiation spot is a diffraction limited spot. In some examples, aberration can be present in the Fl-collection optics and the Fl light can couple to the fiber having a core diameter ~0.1 mm-~0.6 mm in diameter.

In some examples, anti-body reagent(s) or marker(s) are applied to specific micro vesicles. Then, fluorescence is detected from coupled micro vesicles (MVs). Compared to a large live cell (e.g., 10 μm diameter), MVs have a much smaller particle surface and volume. Assuming a sphere shape, values are as given in Table 1.

TABLE 1

| Particle Diameter | Diameter Ratio | Surface Ratio | Volume Ratio |
|---|---|---|---|
| 10 um | 1.0 | 1.0 | 1.0 |
| 1 um | 1/10 | 1/100 | 1/1,000 |
| 0.1 um | 1/100 | 1/10,000 | 1/1,000,000 |
| 0.01 um | 1/1,000 | 1/1,000,000 | 1/1,000,000,000 |

For example, if 1,000,000 conjugated anti-bodies bind on a 10 um size, 0.1 μm-size cell, 1,000,000×1/10,000=100 dye molecules bind to a 0.1 μm microvesicle.

Under irradiation, e.g., laser light, dye molecules emit photon(s) by photon excitation, e.g., to a higher energy state, and decay, e.g., back to a ground state. Photon ratio, QE (quantum efficiency) is emitted photons divided by excited photons. Photon energy is E=1.24/λ(eV).

For some dye molecules, once the molecule is excited and the photon emitted, the dye molecule may be quenched by a photobleaching effect. Further photons will not be emitted by that molecule, in some examples. Therefore, some examples herein include detecting single-photon pulses in order to obtain data from dye molecules before they are photobleached.

Therefore, some examples provide exposure to fresh dye molecules over time to improve system response. Some examples do this using a flying spot, e.g., by scanning irradiation across a sample containing dyed antibodies conjugated to targets. Some examples include rotating a substrate holding the samples to move samples and irradiation with respect to each other. Some examples including moving a substrate linearly. Some examples include moving targets, e.g., using a flow of carrier fluid.

In some examples, in order to excite a target (e.g., a microvesicle or other micro particle) with sufficient intensity and without overlapping other nearby targets, a focused small laser spot is used. In some examples, a flow cell is used.

In a tested example, at 1 m/s scanning velocity, a pulse width was substantially equal to FWHM spot size: 240 nm, or 240 ns at 1 m/s, using a BLU-RAY laser spot of λ=405 nm. The measurement time per particle was ~0.25 μs/particle. In some examples, the irradiation spot has a diameter<2 μm FWHM.

In some examples, the fluorescence signal is detected by detection of single photons without averaging. In some examples, detected photons are averaged with an FWHM time constant τ≈DFWHM/v. DFWHM is the diameter, e.g., in meters or microns, at FWHM.

In some examples, high-NA optics are used to improve collection efficiency. In some examples, optics having low auto-fluorescence are used to reduce noise photons. Examples herein can provide high-speed single photon detection with low dark counts. Detecting single photons of various wavelengths permits performing multi-photon energy spectrum analysis, e.g., to provide histograms, e.g., of photon count as a function of, e.g., wavelength, photon energy, or detector channel.

Figure 7:
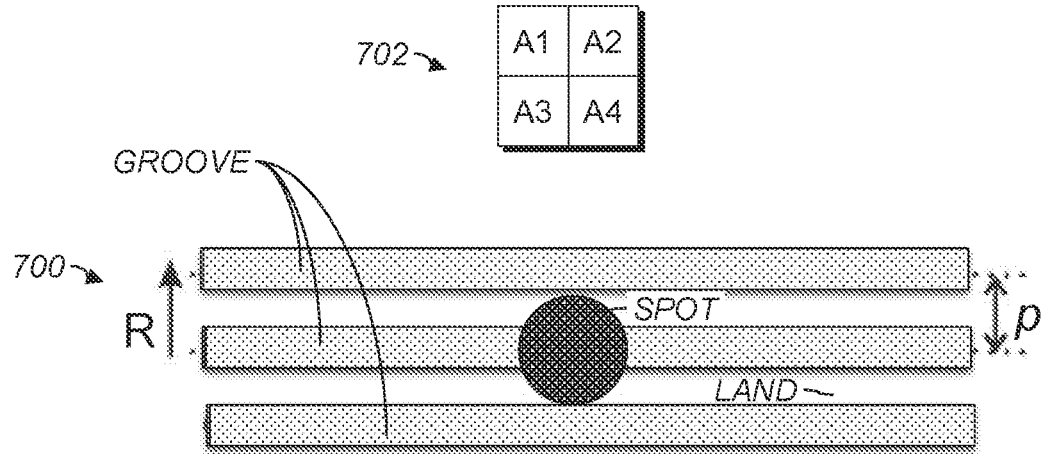
FIG. 7 shows example measurement techniques.
Figure 12:
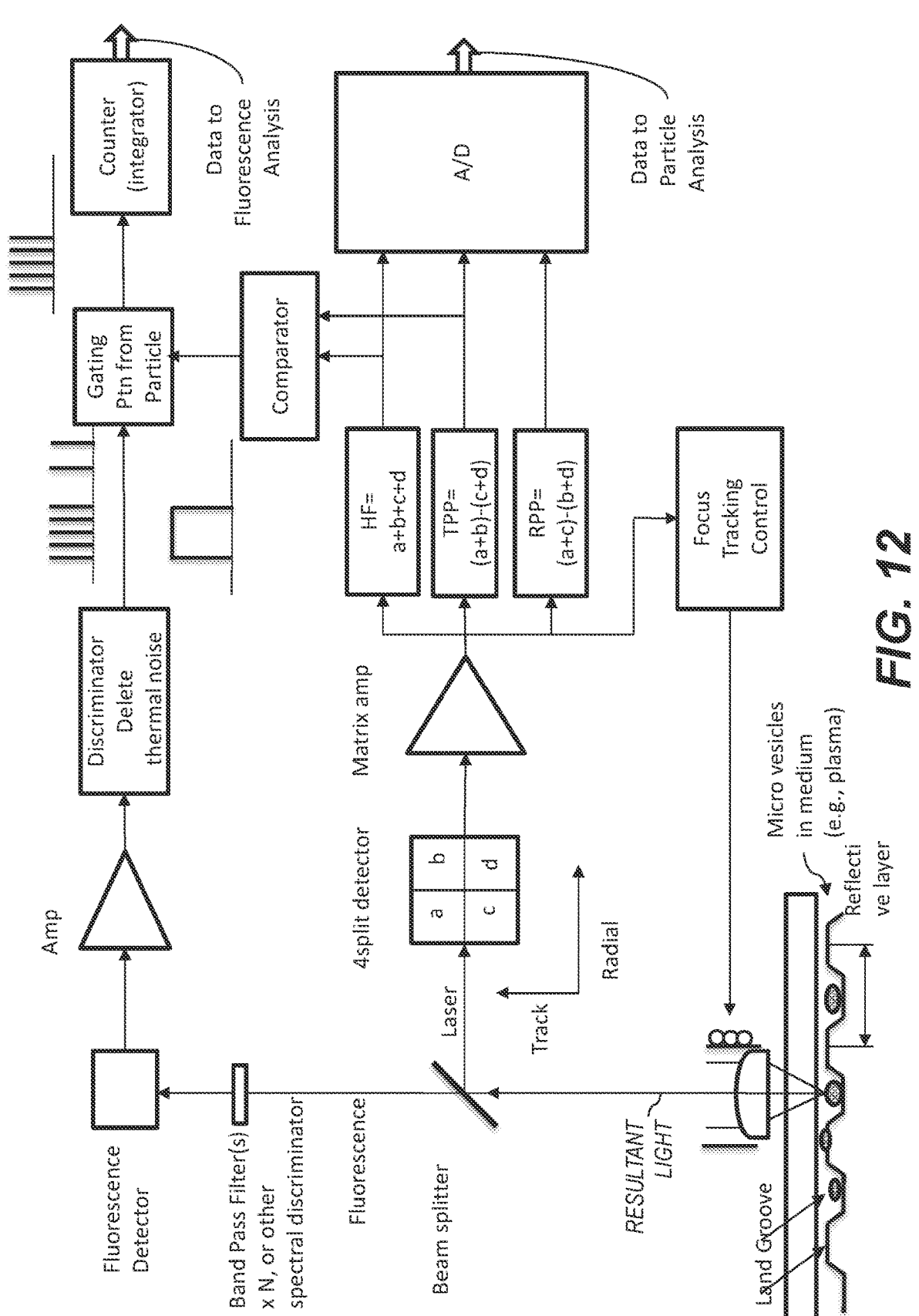
FIG. 12 shows components of an example measurement system, including gating components.
Figure 13:
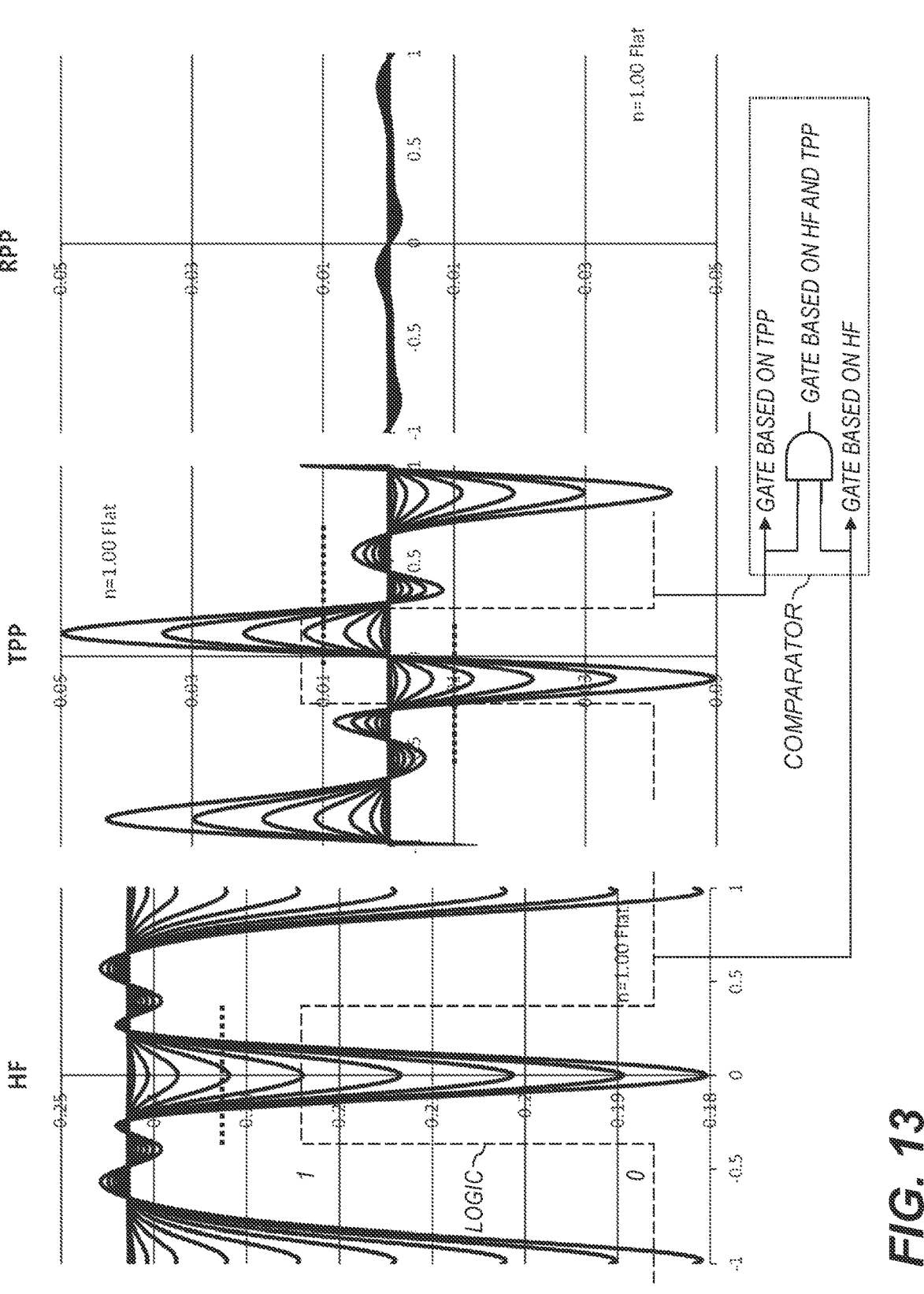
FIG. 13 shows simulated tracking signals and example gating components of an example measurement system.

FIG. 7 shows example measurement techniques. A laser spot irradiates the rotating disk, or otherwise scans or moves relative to the disc, other LOC, or other substrate. As used herein, descriptions of LOC embodiments can apply to disk or other LOC configurations. The laser spot can track at a fixed radial position or a fixed radial rate ("no tracking"), or can be controlled to follow a land ("on-land" tracking) or a groove ("in-groove" tracking). In the illustrated example, the spot follows the groove. A four-way split photodetector (or two two-way split photodetectors orthogonal to each other, or another arrangement of quadrant photodetectors) detects laser light reflected off the disc in four quadrants, A1-A4. The sum of the detected light is called the "HF" signal. Considering the direction of travel of the laser spot with respect to the track as a "frontward" direction, the difference between frontward and rearward halves of a split photodiode (e.g., A1+A3–(A2+A4)) is referred to as a tangential push-pull ("T-PP") signal. The difference between left and right halves of a split photodiode when viewed facing frontward (e.g., A1+A2–(A3+A4)) is referred to as a radial push-pull ("R-PP") signal. The radial push-pull signal indicates how closely the spot is following the track and can be used as an input to a control loop that adjusts the radial spot position to follow the track. HF and push-pull ("PP") signals can both be used to detect targets. Signal-measurement techniques and tracking structures described in U.S. Publication No. 2001/0000696, incorporated herein by reference, and noted above can be used in conjunction with measurement hardware and techniques herein in various examples. Example HF and T-PP signals are shown in FIGS. 12 and 13.

In some examples, the HF signal is modulated by particles of a sufficiently large size (depending on irradiation wavelength, irradiation spot size, and grating pitch/reflectivity). The HF signal can be processed to detect larger cells and particles. Example HF and PP signals indicating detection of targets are shown in FIGS. 9 and 12.

If all targets are in grooves on the disc, in-groove tracking is sufficient. In some examples, on-land tracking can be used to detect large particles that may be located on lands, e.g., because they are too big to fit in the grooves. Measurements can be taken with both in-groove and on-land tracking and the results combined.

Figures 8, 9:
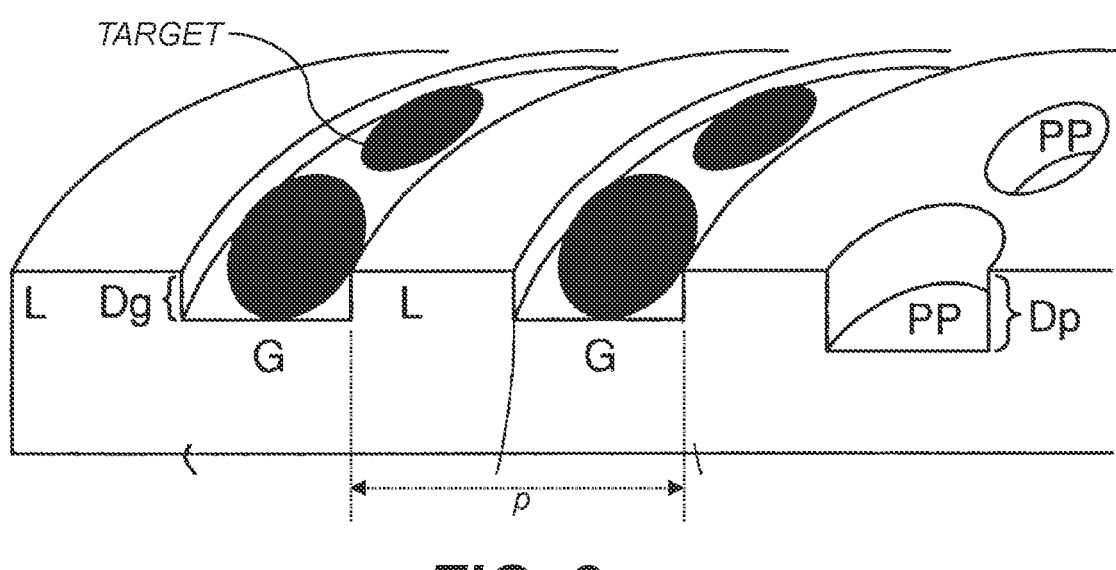
FIG. 8 is an example perspective and cross-section of a disc.
FIG. 9 shows measured data.

FIG. 8 shows a schematic perspective and cross-section of a portion of a disc or other LOC having lands L between grooves G of depth Dg. Targets (black) are in the grooves. In some examples, the groove depth is substantially equal to $\lambda/(8n)$ to increase magnitude of the radial PP signals from the phase grating. In some examples, the track pitch p is set to $\geq 2\times$ the size of targets to be detected. FIG. 8 shows a nonlimiting example configuration of grooves G. An individual groove G can be straight or curved, or can have both straight segments and curved segments. The grooves G can be connected, e.g., as part of a spiral, or can be separate. An individual groove G can have a substantially constant cross-sectional profile (e.g., depth, width, and area), but this is not required.

FIG. 9 shows measured data of a tested example. A laser wavelength $\lambda=405$ nm, a lens with numerical aperture NA=0.85, and a disc with a cover thickness of 0.1 mm were used. Other $\lambda$, NA, and cover-thickness values can also or alternatively be used. Lower $\lambda$ or higher NA values permit detecting smaller targets than higher $\lambda$ or lower NA values do. See also FIGS. 12 and 15.

In FIG. 9, HF and radial PP signals are shown. The bottom half is a magnification of the indicated portion on the top half. The dashed white box shows signals that were measured of a target. The amplitude of modulation of the measured Optical Phase Detection (OPD) signal, compared to (e.g., divided by) the peak-to-peak excursion of that signal, is correlated with the optical path length $\Delta n \times d$ of the target, where $\Delta n$ is the refractive-index difference between the particle and the medium around it, and d is the size of the particle (e.g., mean diameter). In some examples, $\Delta n$ is measured with reference to the polymer material of the disc. In some examples, the medium is selected to have a different refractive index than the disc and to have a different refractive index than the particles.

Figure 10:
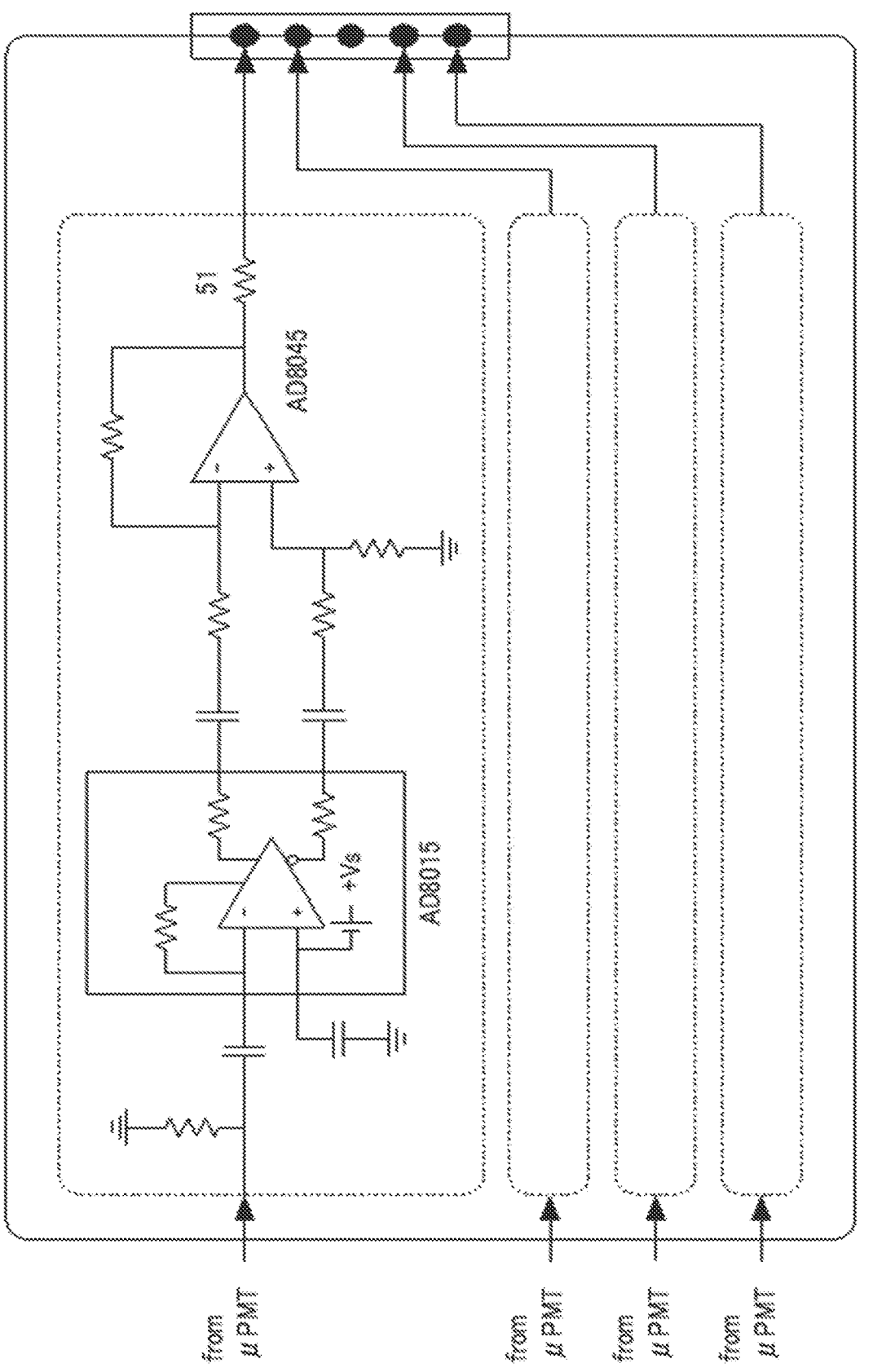
FIG. 10 shows components of an example amplifier.

FIG. 10 shows an example transimpedance amplifier useful with various examples. The illustrated example amplifier has a 70 MHz bandwidth (BW) and connects to an A/D converter input. In some examples, tested micro-photomultiplier tubes ($\mu$PMTs) with an example I-V amp achieved 100 MHz BW with 5 ns pulse width. In some examples, an I-V amp with a 70 MHz lowpass filter (LPF) can have an 8 ns FWHM.

In some examples, a gating signal is produced based at least on the HF and T-PP signals. Further details are discussed below with reference to FIGS. 12 and 13. In some examples, a gating function is used to distinguish signal photons from thermal-noise photons or other photons produced by substances other than target dyes or other chromophores capable of associate with targets.

Some experiments were performed to test various examples described herein. Some experiments detected a 100 nm gold (Au) nanoparticle. Some experiments detected 50 nm Au nanoparticles or 30 nm Au nanoparticles. A reflective phase grating and focused scanning spot together provide effective detection of targets, e.g., vesicles or nanoparticles. Targets can also be detected using a focused scanning spot in combination with a flow cell.

Some experiments indicate particles as small as ~10 nm can be detected. Some experiments show that the number of particles is countable by the number of pulses, e.g., of the HF signal. Some experiments show that various aspects can estimate particle size using the pulse width and modulation depth of the HF and PP signals. Various aspects receive as input measured, estimated, or computed refractive indices of the medium, e.g., blood plasma or air, and target and use those refractive indices in computing sizes of the targets. Various aspects use fluorescent dyes or a pre-check to distinguish targets from, e.g., surface defects, dust particles, non-target air bubbles, or other microstructures that are not targets to be measured. In some examples, the pre-check includes measuring data before applying targets to the reflective phase grating. This permits detecting, e.g., nanometer-scale defects in the substrate.

Various aspects, including some aspects shown in FIG. 1-8, 11, 12, 15, or 16, include a microvesicle measurement platform having a reflective phase grating arranged in or adjacent to a microfluidic channel, a sample-delivery system, an irradiation system, and a detection system. Using a reflective grating provides effective optics and doubles phase detection compared to some prior schemes. Using a reflective grating also permits using low-cost manufacturing techniques developed for CD, DVD, and BLU-RAY discs (providing, e.g., 3 s per disc manufacturing time). The irradiation system can include one or more lenses or scanners to provide a focused scanning laser spot. The detection system can include on or more photomultiplier tubes (PMTs) or other optical detectors. PMTs can be used, e.g., to detect fluorescence from targets or from dyes or other fluorochromes in, on, or associated with targets. The sample-delivery system can include a filter, e.g., to separate red blood cells from plasma so that targets in the plasma, e.g., microvesicles, can be measured apart from the red blood cells.

In various aspects, targets such as nanoparticles are detected as HF and PP signal perturbations caused by optical path differences such as different optical path length. In various aspects, the detected HF pulse width and tangential PP signal modulation are used to determine tangential particle size. In various aspects, radial PP signal modulation is used to determine radial particle size. Various aspects use radial PP together with HF or tangential PP (or both) to provide 2D data of targets.

Various aspects include a substrate including a microfluidic channel on, over, or adjacent to a reflective phase grating. The microfluidic channel can have a height (away from the grating), e.g., of <5 μm. These aspects can be embodied in, e.g., LOC structures. LOCs can include rigid, semi-rigid, or flexible substrates.

Various aspects, e.g., of LOCs, include disposable chips having sample-processing structures such as cell-separation structures, staining structures, filtering structures, measurement structures, and waste-retention structures. Such aspects can be used, e.g., in clinical applications. For example, LOCs can be used to perform high-volume analysis of samples from many patients in a hospital, or many customers of an analysis lab.

Various aspects include an optical assembly including a tracking system for focusing and tracking of a laser spot, e.g., a focused laser spot, on a reflective grating. The tracking system can operate in rotation, e.g., for disk-shaped LOCs, or in traverse (e.g., X-Y axis), e.g., for slide-glass-shaped LOCs.

In some examples, microvesicles or other targets adhere to lands or grooves of a disc or LOC, e.g., due to electric field interactions, van der Waal's forces, surface tension and wetting of the surface of the disc, or other microscale interactions.

Various aspects include acts to enhance refractive index difference between particles and medium. For example, a sugar solution can be selected to have a different refractive index than the targets of interest. The targets of interest can include, e.g., molecules or other targets of at least one predetermined type, e.g., targets to which selected antibodies can bind. In some examples, air is used as a medium so n≈1. In some examples, a polymer medium is used and the wavelength of light is selected to achieve a desired $n_\lambda$ of the polymer. In some examples, water or another aqueous medium is used and solutes are added to adjust refractive index n or dielectric constant k of the medium. For example, a 10% glucose solution can have a refractive index of 1.3477, a 20% glucose solution 1.3635, or a 60% glucose solution 1.4394. In some examples, the refractive index of the medium can be varied and measurements can be taken at various medium n values, e.g., continuously or in discrete steps. A refractive index of the medium can be selected, e.g., from those tested, that provides a selected signal-to-noise ratio or other metric of measurement quality.

In some examples, statistics of the measured data are gathered to, e.g., extrapolate from measurements of fewer than all of the particles. For example, average particle size can be computed from measurements of a selected number of particles.

Various aspects include data acquisition and analysis software for detecting variations in the light reflected off a reflective phase grating.

Various aspects include structures or techniques for fluorochrome staining of microvesicles or other targets. These aspects can be used to identify the origins, compositions, or identities of particles, or to distinguish particles from background noise such as electrical noise. Electrical noise can include, e.g., shot noise in the photodetectors measuring light reflected by the phase grating.

Various aspects include scanning of phase gratings, focused laser spots, or both. Scanning can be performed by mechanical scanning devices such as disk rotation systems or X-Y stages, or by optical scanning devices such as galvanometer motors ("galvos") or beam deflectors.

Various aspects include separating a detected signal into servo bandwidth signals and detected particle signals. This can be done, e.g., using split photodetectors or using filters on specific temporal-frequency ranges.

Various aspects include one or more of the below-listed properties.

A. Effective Phase grating depth of λ/8n

B. Grating pitch p>λ/2NA.

C. Detection optics: λ=405 nm, NA=0.85, cover thickness=0.1 mm, focused spot size=0.39 μm (1/e2), p>240 nm, or any combination of those.

D. p=1.6 μm, p=0.74 μm, or p=0.32 μm

E. A disc structure having a spiral groove in which successive turns are separated by the pitch p.

F. A disc structure in which the reflective phase grating is arranged around a center of the disc between about 38 mm from the center and about 42 mm from the center.

G. A measurement zone with no grooves, e.g., a mirror or substantially flat metal surface of a disc or other LOC H. Phase grating depth ~40 nm and pitch p=500 nm.

I. Land & groove aspect ratio is 50:50. Other ranges can be used, e.g., 60:40 or 40:60.

J. Servo bandwidth<50 kHz and particle signal bandwidth>100 kHz,

K. Data acquisition has sufficient bandwidth (BW) and resolution. E.g., at 1.0 m/s scanning velocity, 10 nm particle is detected as 10 nsec width pulse. Measurement hardware having a bandwidth of 200 MHz (5 ns) can be used in this example. In some examples, signal rise time can be computed as 0.35/BW. Signals with a 5 ns rise time can therefore be measured with hardware having at least 70 MHz bandwidth.

L. Fluorescence analysis of micro particles with a conjugated anti-body.

M. Fluorescence analysis of microparticles stained with a dye. For example, proteins can be stained with FITC, lipids with Nile red, or DNA with Hoechst 33342. Other dyes can be selected for use depending on the excitation wavelength.

N. Excitation by a focused flying laser spot with smaller than 2 μm FWHM.

O. Applying wavelength or photon energy spectrum apparatus between micro particles and detectors—dichroic mirror, grating or prism spectro meter, filter, etc.

P. Detecting single photon pulses without averaging, e.g., less than 20 ns width Q. Detecting photon pulses with time constant ~τ=DFWHM/v R. Distinguishing signal & noise photons by gating with HF/Push-Pull signals from particles, e.g., HF and T-PP.

S. Analyzing numbers of single photons by wavelength/photon energy, e.g., by histograms.

T. Investigating micro particle fluorescence by single photon spectroscopy.

U. Measuring microvesicles.

V. Detecting fluorescence and providing imaging for micro and nano particles.

In some examples, one focusing point is sufficient since the number of microvesicles is relatively high. In other examples, multiple focusing points are used (e.g., in-groove and on-land).

In view of the foregoing, various aspects provide effective detection or size measurement of small particles. A technical effect of various aspects is to measure physical properties of a sample, e.g., a sample of blood or another bodily fluid.

Figure 11:
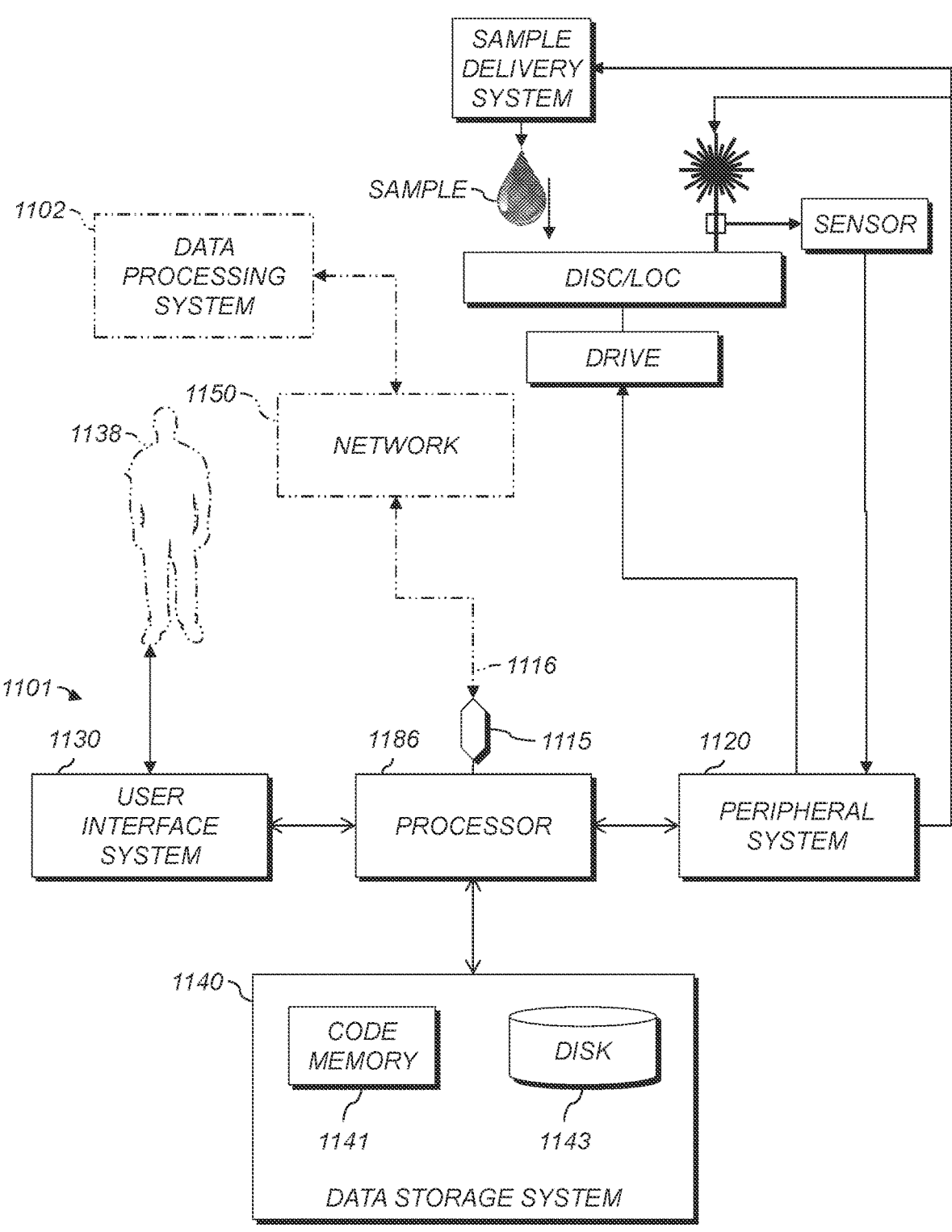
FIG. 11 is a diagram showing the components of an example measurement system, including data-processing components useful with various examples.

FIG. 11 is a high-level diagram showing the components of an exemplary data-processing system 1101 for analyzing data and performing other analyses described herein, and related components. The system 1101 includes a processor 1186, a peripheral system 1120, a user interface system 1130, and a data storage system 1140. The peripheral system 1120, the user interface system 1130, and the data storage system 1140 are communicatively connected to the processor 1186. Processor 1186 can be communicatively connected to network 1150 (shown in phantom), e.g., the Internet or a leased line, as discussed below. Systems shown in FIGS. 4-6, 10, and 12, can include one or more of systems 1186, 1120, 1130, 1140, and can connect to one or more network(s) 1150. Processor 1186, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 1186 can implement processes of various aspects described herein. Processor 1186 and related components can, e.g., carry out processes for receiving a sample on a substrate having a reflective phase grating thereon or thereover, irradiating the sample with a focused spot of light while traversing over the substrate, detecting variations in reflected light, and determining properties of a target (e.g., presence, size, orientation) using the detected variations. Processor 1186 and related components can, e.g., carry out processes for making discs or LOCs by controlling mastering equipment to make stampers, mold discs or LOCs using stampers, sputter discs or other LOCs, or apply cover materials to discs or LOCs.

Processor 1186 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise.

The phrase "communicatively connected" includes any type of connection, wired or wireless, for communicating data between devices or processors. These devices or processors can be located in physical proximity or not. For example, subsystems such as peripheral system 1120, user interface system 1130, and data storage system 1140 are shown separately from the data processing system 1186 but can be stored completely or partially within the data processing system 1186.

The peripheral system 1120 can include or be communicatively connected with one or more devices configured or otherwise adapted to provide digital content records to the processor 1186 or to take action in response to processor 186. For example, the peripheral system 1120 can include digital still cameras, digital video cameras, cellular phones, or other data processors. The processor 1186, upon receipt of digital content records from a device in the peripheral system 1120, can store such digital content records in the data storage system 1140.

In the example shown, peripheral system 1120 is connected to a drive, a sensor, a laser, and a sample-delivery system. The drive spins the disc (in other configurations, the drive can scan a laser across a stationary LOC), e.g., as done to spin BLU-RAY discs. The sample-delivery system applies to the disc or other LOC fluid samples to be measured for the presence or properties of targets. For example, the sample-delivery system can include an automated pipette or other metering system for applying a selected amount of sample. The laser irradiates the disc or other LOC and the sensor measures reflected light (illustrated as coming from a beam-splitter, though other configurations can be used, e.g., a laser at an angle to the substrate other than normal). Processor 1186 and peripheral system 1120 coordinate these components to measure the samples and target(s) therein. Other examples of components that can be operated by processor 1186 are shown in FIGS. 4-6, 10, and 12. Various nonlimiting examples of LOCs that can be used with components shown in FIG. 11 are shown in FIGS. 15 and 16.

The user interface system 1130 can convey information in either direction, or in both directions, between a user 1138 and the processor 1186 or other components of system 1101. The user interface system 1130 can include a mouse, a keyboard, another computer (connected, e.g., via a network or a null-modem cable), or any device or combination of devices from which data is input to the processor 1186. The user interface system 1130 also can include a display device, a processor-accessible memory, or any device or combination of devices to which data is output by the processor 1186. The user interface system 1130 and the data storage system 1140 can share a processor-accessible memory.

In various aspects, processor 1186 includes or is connected to communication interface 1115 that is coupled via network link 1116 (shown in phantom) to network 1150. For example, communication interface 1115 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WIFI or GSM. Communication interface 1115 sends and receives electrical, electromagnetic, or optical signals that carry digital or analog data streams representing various types of information across network link 1116 to network 1150. Network link 1116 can be connected to network 1150 via a switch, gateway, hub, router, or other networking device.

In various aspects, system 1101 can communicate, e.g., via network 1150, with a data processing system 1102, which can include the same types of components as system 1101 but is not required to be identical thereto. Systems 1101, 1102 are communicatively connected via the network 1150. Each system 1101, 1102 executes computer program instructions to, e.g., carry out measurements as described herein.

Processor 1186 can send messages and receive data, including program code, through network 1150, network link 1116, and communication interface 1115. For example, a server can store requested code for an application program (e.g., a JAVA applet) on a tangible non-volatile computer-readable storage medium to which it is connected. The server can retrieve the code from the medium and transmit it through network 1150 to communication interface 1115. The received code can be executed by processor 1186 as it is received, or stored in data storage system 1140 for later execution.

Data storage system 1140 can include or be communicatively connected with one or more processor-accessible memories configured or otherwise adapted to store information. The memories can be, e.g., within a chassis or as parts of a distributed system. The phrase "processor-accessible memory" is intended to include any data storage device to or from which processor 1186 can transfer data (using appropriate components of peripheral system 1120), whether volatile or nonvolatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 1140 can be a tangible non-transitory computer-readable storage medium, i.e., a non-transitory device or article of manufacture that participates in storing instructions that can be provided to processor 1186 for execution.

In an example, data storage system 1140 includes code memory 1141, e.g., a RAM, and disk 1143, e.g., a tangible computer-readable rotational storage device or medium such as a hard drive. Computer program instructions are read into code memory 1141 from disk 1143. Processor 1186 then executes one or more sequences of the computer program instructions loaded into code memory 1141, as a result performing process steps described herein. In this way, processor 1186 carries out a computer implemented process. For example, steps of methods described herein, blocks of the flowchart illustrations (e.g., FIG. 14) or block diagrams herein, and combinations of those, can be implemented by computer program instructions. Code memory 1141 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code ("program code") stored on a computer readable medium, e.g., a tangible non-transitory computer storage medium or a communication medium. A computer storage medium can include tangible storage units such as volatile memory, nonvolatile memory, or other persistent or auxiliary computer storage media, removable and non-removable computer storage media implemented in any method or technology for storage of information such as computer-readable instructions, data structures, program modules, or other data. A computer storage medium can be manufactured as is conventional for such articles, e.g., by pressing a CD-ROM or electronically writing data into a Flash memory. In contrast to computer storage media, communication media may embody computer-readable instructions, data structures, program modules, or other data in a modulated data signal, such as a carrier wave or other transmission mechanism. As defined herein, computer storage media do not include communication media. That is, computer storage media do not include communications media consisting solely of a modulated data signal, a carrier wave, or a propagated signal, per se.

The program code includes computer program instructions that can be loaded into processor 1186 (and possibly also other processors), and that, when loaded into processor 1186, cause functions, acts, or operational steps of various aspects herein to be performed by processor 1186 (or other processor). Computer program code for carrying out operations for various aspects described herein may be written in any combination of one or more programming language(s), and can be loaded from disk 1143 into code memory 1141 for execution. The program code may execute, e.g., entirely on processor 1186, partly on processor 1186 and partly on a remote computer connected to network 1150, or entirely on the remote computer.

FIG. 12 shows a block diagram of an example gating system. Resultant light is divided between the split photo-detector and the fluorescence detector, e.g., as described above with reference to FIG. 4. HF and T-PP signals are produced and provided to a comparator. The comparator provides a gating function, e.g., by thresholding or detecting edges of, e.g., the HF or T-PP signals from the split photo-diode. Various examples of comparators are discussed below with reference to FIG. 13.

A signal from a fluorescence detector, e.g., a µPMT, can be passed through a discriminator. The discriminator can remove noise, e.g., thermal noise. In some examples, the discriminator removes pulses having a pulse height (e.g., measured in volts) smaller in magnitude than a selected lower level of discrimination (LLD). In some examples, the discriminator removes pulses having a pulse height larger in magnitude than a selected upper level of discrimination (ULD). The resulting pulses are gated by the gating function, e.g., by passing pulses only when the gating function has a high logic value or other gate-open value. The resulting pulses are counted. The counts of pulses can then be provided for fluorescence analysis.

FIG. 13 shows simulated tracking signals, in this example HF, T-PP and R-PP signals. In the example plots, a particle is centered at 0 on the X-axis. Units on both axes or arbitrary. The axes can be, e.g., microns on the X-axis and volts on the Y-axis. The curves show respective, different particle sizes from 10 nm-100 nm.

On the left-hand, HF plot, the dotted line shows a threshold. In some examples, a gating signal corresponding to the HF signal has a true logic value (e.g., a 1 value) when the HF signal is below the threshold, as represented by the dashed line. In other examples, the gating signal corresponding to the HF signal has a true logic value when the HF signal is above the threshold, within a specified range, or outside a specified range. In an example, the gate is open (true logic level) during the 240 ns FWHM of a laser pulse.

On the center, T-PP plot, the T-PP signal has a negative excursion when beginning to cross the particle and a positive excursion when leaving the particle. The dotted lines show thresholds for the excursions. In the illustrated example, the logic signal (dashed) corresponding to the T-PP signal has a true logic value between the low-going crossing of the threshold in the negative excursion and the low-going crossing of the threshold in the positive excursion.

In some examples, the gate is open (photons are counted) when the HF logic signal has a true logic value, when the T-PP logic signal has a true logic value, or when both the HF and T-PP logic signals have true logic values. These examples are illustrated in the box labeled "Comparator."

In some examples, the size of a particle (or other target) is determined from the height and width of the HF pulse, e.g., by measuring levels of the HF pulse, ramp rates of the HF pulse, or FWHM of the HF pulse. For example, D-FWHM or the duration of the true logic level on the HF logic signal can indicate particle size. In some examples, the size of a particle is determined from the duration of the true logic level on the T-PP logic signal, or from the heights or widths of the excursions on the T-PP signal. In some examples, the lateral position of the particle in the groove or on the land is determined using the pulse height or ripple of the R-PP signal.

FIG. 14 shows a flowchart of example methods 1400 of measuring targets. Steps of FIG. 14 or other methods described herein can be performed in any order except when otherwise specified, or when data from an earlier step is used in a later step. Exemplary method(s) described herein are not limited to being carried out by components particularly identified in discussions of those methods.

At 1405, particles of selected size range(s) can be removed from a sample. For example, samples can be centrifuged, filtered, fractionated, or otherwise divided into portions based on particle size. For example, large particles can be removed from a sample to permit analysis of small particles (or other targets) remaining in the sample. Block 1405 can be followed by block 1420.

At 1410, a reflective phase grating can be constructed or arranged in, on, or over a substrate. For example, grooves can be etched into a slide, or a BLU-RAY or other lab-on-disc can be prepared using stamping with a PTM master as described herein.

At 1420, a sample can be applied to, disposed over, or received at the reflective phase grating. For brevity, the phrase "applying a sample to the reflective phase grating" and similar phrases, as used herein, includes any or all of the above options. A sample can be applied to (e.g., disposed over or received at, and likewise throughout) the reflective phase grating or other reflective grating, e.g., using a micropipette. The sample can be transported to or across the reflective phase grating or other sensing region at least partly by capillary action, e.g., as discussed herein with reference to FIG. 18.

At 1430, the reflective phase grating can be irradiated, e.g., using a laser, lamp, LED, or other light source. Focusing or collimating optics can additionally be used.

At 1435, presence-related signals can be measured. Presence-related signals can include HF, R-PP, T-PP, or other signals useful for determining whether or when a target is being irradiated. In some examples, before, concurrently with, or in addition to measuring fluorescence, non-fluorescence or other additional signal(s) are measured to determine, e.g., presence, size, shape, or volume of a target or other particle being irradiated. In some examples, the number of particles (or other targets) or the sizes and shapes of individual particles are measured, and fluorescence data from some of the particles are measured, e.g., to determine the origins of the particles.

In some examples, HF or PP signals are measured in a reference area. The reference area can include, e.g., a mirror (non-grooved) area of a disc or LOC, or an area with grooves but without samples or targets. Block 1435 can include measuring the HF or PP signals and determining a variation of the measured signal from the previously-measured signal in the reference area. In some examples, variations between a reference signal and a corresponding signal measured in a sample indicate the presence of targets, EVs, or other microparticles in the sample, as discussed above with reference to FIGS. 5-9.

At 1440, emitted fluorescence or other reflected, transmitted, emitted, or scattered light can be measured, e.g., using a μPMT or other sensors described herein. This can be done, e.g., when or during a period in which the presence-related signals indicate a target is being irradiated. This can reduce mis-identification as target-related of photons not from a target.

At 1442, detection signals from a μPMT or other sensors can be gated. For example, gating can be performed as discussed above with reference to FIGS. 12 and 13. Although shown as part of block 1440 for purposes of explanation, functions performed at block 1442 can be performed before or after functions performed at block 1440. For example, gating can be performed in the analog domain on μPMT or amplifier (FIG. 10) outputs, or can be performed in the digital domain on digitized representations of those outputs.

At 1445, the location of irradiation ("irradiation spot") can be moved, i.e., relative motion of an irradiation spot and the reflective phase grating can be caused. For example, a laser can be redirected, e.g., rasterized across the grating, the sample, or a target in the sample. Additionally or alternatively, the grating, the sample, or the target can be moved, e.g., by the spinning of a disc over or under a laser or other irradiation source substantially fixed in tangential position with respect to the axis of rotation of the disc. A spot-traversal system can cause such relative motion, and can include one or more of the following: rasterizers; polygons or other movable mirrors; mirror or micromirror arrays; fixed mirrors; rotational, linear, XY, or XYZ stages or drives; lenses; or gratings.

At 1450, data of the detected fluorescence can be processed to detect targets or measure properties of targets, e.g., as described herein. For example, detected photon signals can be gated, e.g., as described herein. Example gating can be performed based at least in part on HF and T-PP signals. Pulse heights can be measured and recorded, e.g., in histogram bins, or pulses can be counted.

FIG. 15 shows example of a lab-on-chip device (LOC), e.g., as discussed herein with reference to FIGS. 1-8. The LOC is an example of a sample carrier, a device for retaining or transporting a sample for measurement as described herein. In some examples, as graphically represented by the double-headed "light" arrow, a target in a detection region (also referred to herein as a "detection zone," as shown, or as a "sensing region") is irradiated by a focused spot of light. The focused spot of light can have a range of irradiation wavelengths, of which the peak power, or mean, median, or other representative wavelength can be an irradiation wavelength. Resultant light is detected concurrently with or subsequent to irradiation. Resultant light can include, but is not limited to, light reflected by the target, light emitted by the target, or light reflected or diffracted by a reflective surface, e.g., a reflective grating, in the detection region. References herein to detecting or measuring resultant light can include producing signals, e.g., analog or digital electrical signals, representing at least some of the resultant light, unless expressly indicated. In some examples, target(s) can be carried in a fluidic sample.

In some examples, dimension A can be ~1.1 mm, dimension B can be ~1 μm or ~2 μm, dimension C can be ~100 μm, or dimension D can be ~500 μm. In some examples, a reflective surface, e.g., a reflective grating, can be directly overcoated with a layer, e.g., a clearcoat protective layer. Targets, e.g., in a fluid sample, such as a liquid sample, can be deposited onto the reflective layer or the clearcoat layer for measurement.

The fluid sample can be added through a sample inlet ("INLET"), e.g., after removing a seal ("SEAL"). The inlet can be associated with a substrate of the LOC, e.g., can be arranged in, on, over, or through the substrate. The inlet can include or be associated with a filter ("FILTER"). The inlet can convey at least some of the fluid sample, in the direction indicated by the open arrow, to a fluid channel ("CHAN- NEL") configured to convey at least some of the fluid sample towards (e.g., over) the reflective surface. The reflective surface can be associated with the substrate of the LOC, e.g., can be arranged on, in, or over the substrate. The sample inlet can be fluidically connected to the channel. As used herein, components that are "fluidically connected" are structured and arranged to permit a relevant fluid to flow between them. Fluidically connected components can be directly connected, or can be connected via intermediaries (e.g., as inlet area 806 and 810, FIG. 8 are fluidically connected via fluid channel 808, as discussed below).

Table 2 lists attributes of sample carriers according to various examples herein. This disclosure expressly contemplates each possible combination of attributes formed by selecting one attribute value from each row of Table 2. Sample carriers can include, e.g., disc, slide, or chip formats, as described herein.

TABLE 2

| Category | Attributes |
| --- | --- |
| Reflective Surface | "Mirror" (substantially flat); grating |
| Cover between optics and sample | Present; absent |
| Cover material | Glass; plastic |
| Target carrier | vacuum; air; dried formerly-liquid sample; stationary liquid; flowing fluid |
| Target type | Homogeneous refractive index; heterogeneous refractive index |
| Material between reflective surface and target | Present; absent |
| Format | Disc; slide; chip |

In addition, this disclosure expressly contemplates detecting resultant light, e.g., light reflected by or emitted from or over a sample carrier having any combination of attributes listed in Table 2. This disclosure expressly contemplates detecting such light using detection systems such as those listed in Table 3, e.g., using respective systems according to each possible combination of one attribute value per row. That is, any selection of one attribute per row of Table 2 can be combined with any selection of one attribute per row of Table 3. In Table 3, "focusing" refers to adjusting spot position substantially normal to a sample carrier, and tracking refers to adjusting spot position substantially laterally with respect to a sample carrier, e.g., to track a groove such as those shown in FIGS. 2-7.

TABLE 3

| Category | Attributes |
| --- | --- |
| Emission wavelength | Ultraviolet; visible; infrared |
| FWHM | Specific values for, e.g., Gaussian or flat-top profiles (see, e.g., Table 4) |
| Numerical aperture | Specific value (see, e.g., Table 4) |
| Type | Laser; collimated beam |
| Focusing | Present; absent |
| Tracking | Present; absent |
| Detection wavelength | Substantially the same as an emission wavelength; substantially different from an emission wavelength or from any emission wavelengths |
| Motion | Stationary irradiation spot; moving irradiation spot |

Examples of specific attribute values are shown in Table 4. This disclosure expressly contemplates using any of the attribute values shown in Table 4, or any combination thereof, with any combination of corresponding attributes listed in Table 2 or Table 3. In some examples, the emission wavelength can be, e.g., an irradiation wavelength as described herein. The emission wavelength can be selected to excite fluorescent emissions from a target, though this is not required. Fluorescence is described herein with reference to, e.g., FIG. 13-15, 19, or 26.

TABLE 4

| Category | Attributes |
| --- | --- |
| Cover material | Polycarbonate; glass |
| Target carrier | Flowing liquid; flowing gas |
| Material between reflective surface and target | A spin-coating over a reflective grating; a glass or plastic slide having the reflective material on the opposite side from the surface that receives the sample. |
| Format | A microscope slide having a reflective coating; a fluidic chip including a flow cell, flow chamber, or other flow channel. |
| Emission wavelength | 785 nm; 650 nm; 405 nm |
| FWHM | 1040 nm; 557 nm; 245 nm |
| Numerical aperture | 0.45; 0.60; 0.85 |
| Focusing | Using a lens to focus a laser beam on a flow channel |
| Detection wavelength | The wavelength of fluorescence of a dye added to the sample to indicate presence of targets |
| Motion | A substantially stationary irradiation spot used with a flowing fluidic sample; a moving irradiation spot scanned, e.g., raster-scanned or scanned linearly, across a flow channel. |

In some examples, a non-grooved configuration is used. For example, the channel can be a straight-walled channel, e.g., in a glass lab-on-chip, such as shown in FIG. 16. The cross-section of such a device can be as shown in FIG. 15, except with a substantially flat reflective surface. Such a surface is represented graphically by the heavy dotted line in FIG. 15. In some examples, the channel can be, e.g., 1 μm thick, 1000 μm wide, and 8000 μm long, for a volume of 8 nL. The inlet can have a diameter of 4 mm-5 mm. Below the filter, the inlet can narrow to a diameter of 0.5 mm-0.7 mm where the inlet meets the channel.

In some examples, at the left end of the channel, as shown in the figure, the channel can be connected to a fluid sink having, e.g., a diameter of 6 mm, e.g., an area holding 28 nL of fluid. The fluid sink can retain fluid that has passed through the channel.

FIG. 16 shows another example of an LOC 1600. In some examples, LOC 1600 includes multiple fluid tanks, e.g., four tanks 1602, 1604, 1606, and 1608 (or three tanks 1602, 1604, and 1608, or any combination of any number of the four tanks). For example, tank 1602 can include a 20 μL tank to which sample, e.g., blood, is added, e.g., through the top, end, or side of LOC 1600 or tank 1602. In some examples, sample can be added to tank 1602 through an inlet such as that shown in FIG. 15. Tank 1604 can include cell-separation or other filtering features, e.g., micropillars. An example micropillar arrangement is shown in plan in inset 1610, with arrows indicating the direction of sample flow. In some examples, tank 1606 can hold dye(s) or other substances to enhance optical detection of targets. Tank 1608 can be, e.g., a reservoir or waste tank. In some examples, tank 1608 can include an outlet 1612, e.g., configured to connect to a vacuum source.

In detection region 1614, targets (illustrated as dots) can be irradiated. Resultant light from detection region 1614 can be detected. Detection region 1614 can include grooves 1616, graphically represented as lines. FIG. 16 shows example straight grooves 1616, e.g., forming a reflective phase grating, e.g., on an LOC such as a rectangular LOC. Grooves 1616 can have other configurations than straight, e.g., the configurations in FIGS. 17 and 18.

In various examples, a disc or other LOC can have lands L between grooves 1616 of depth Dg. Targets can be in the grooves or on the lands. In some examples, the groove depth Dg is substantially equal to $\lambda/8n$ to increase magnitude of the push-pull (PP) signals from the phase grating. In some examples, the track pitch p is set to at least twice the size (e.g., mean diameter) of targets to be detected. In some nonlimiting example configurations of grooves 1616, an individual groove 1616 can be straight or curved, or can have both straight segments and curved segments. The grooves 1616 can be connected, e.g., as part of a spiral, or can be separate. An individual groove 1616 can have a substantially constant cross-sectional profile (e.g., depth, width, and area), but this is not required.

FIG. 17 shows an example plan view of spiral grooves, forming a reflective phase grating, e.g., on an LOC such as a rectangular LOC. As in FIG. 2, the groove profile is represented by the cross-section in heavy lines.

FIG. 18 shows a schematic plan view of an example lab-on-disc, e.g., as discussed herein with reference to FIG. 1-8, 11, 12, or 15. In some examples, FIG. 18 can represent the bottom view of a lab-on-disc as shown in FIG. 15, as indicated by the "XVIII" marker in FIG. 15. FIG. 18 shows example fluid-handling components of the device. The device can be formed on a BLU-RAY disc blank or similar substrate. The device has one or more fluid inlets ("IN-LET"), e.g., circular inlets having diameters of, e.g., 0.5 mm. Two inlets are shown, but that is not limiting. The inlets can be or include holes through the substrate. The inlets open onto one or more fluid channels ("CHANNEL"). The channels can have flat surfaces (e.g., the dotted line in FIG. 15), or can have grooves and lands (e.g., the reflective grating shown in solid lines in FIG. 15). The channels can be separated by one or more barriers ("BARRIER"). The barriers can have a height, e.g., of 2 µm. The barriers can be formed by applying a patterned bonding layer to the substrate, or by performing surface molding on the substrate. A cover can be applied over the barriers, to form the channels between the substrate, the cover, and the barriers. The cover can have a thickness of 100 µm and can be, e.g., glass or polymer film. The cover can be affixed to the barriers or the substrate, e.g., using adhesive. The barriers can have openings ("OUTLET") to permit air to escape the channels as fluid is added through the inlets, or to permit removing fluid from the channels. In some examples, a fluidic sample is presented at one or more of the inlet(s), e.g., via a syringe, micropipette, or other fluid container. In some examples, the fluidic sample presented at the inlet(s) fills corresponding area(s) of the channel(s) by capillary action.

Channel shapes such as that shown in FIG. 18, and other complex channel shapes (e.g., shapes that do not extend in a substantially straight line from a single inlet), can be used with any of the lab-on-chip or lab-on-disc configurations herein. Relative motion of an irradiation spot and a sample in a channel can be carried out by, e.g., rasterizing or otherwise scanning the irradiation spot across the channel, e.g., using an electro-optical deflector (EOD), an acousto-optic deflector (AOD), or another device such as those described herein with reference to FIG. 21. Additionally or alternatively, the relative motion can be caused by moving the channel under the spot (e.g., by spinning a disc as in FIGS. 3 and 4); causing a fluidic sample to flow along the channel past a stationary or scanning irradiation spot, e.g., as in FIGS. 19-21; or any combination thereof.

FIG. 19 shows an example optical detection system 1900. Resultant light from a flow channel (which can move relative to an irradiation spot, or vice-versa, as indicated by the arrows) is focused by a lens into fiber coupling optics, e.g., tapered fiber coupling optics. The flow channel can be a flow channel of a conventional flow cytometer, e.g., a BECKMAN COULTER FC500. A wavelength disperser ("spectro unit"), e.g., including a toroidal mirror grating or other polychromator, can disperse different wavelengths of light into respective, different optical fibers. For brevity, further processing is shown for only one fiber; however, any number of fibers can be used as described herein. Light from the fiber is provided to an optical detector 1902, e.g., an avalanche photodiode, photomultiplier tube, or silicon photomultiplier. The electrical signal from optical detector 1902 is provided to a capture unit 1904, e.g., including a transimpedance amplifier and an analog-to-digital converter. Each fiber can be connected to a respective optical detector 1902 and associated with a respective capture unit 1904. In some examples, the wavelength disperser can provide, e.g., 42 output fibers ("channels" or "CH") (a "42CH" configuration), each with its own wavelength. Some examples include dichroic beamsplitters, prism optics, or multi-channel PMTs. In some examples, each fiber is connected to a respective optical detector 1902, e.g., an individual detector or an element of a detector array such as a linear CCD. In some examples, each electrical signal from an optical detector 1902 is connected to an input of a multi-channel capture unit 1904, e.g., a 16-bit, 48-channel ADC. In some examples, a capture unit 1904 can include a high-speed TIA or other components providing, e.g., a bandwidth in the GHz range (e.g., 100 MHz-1 GHz).

Figure 20:
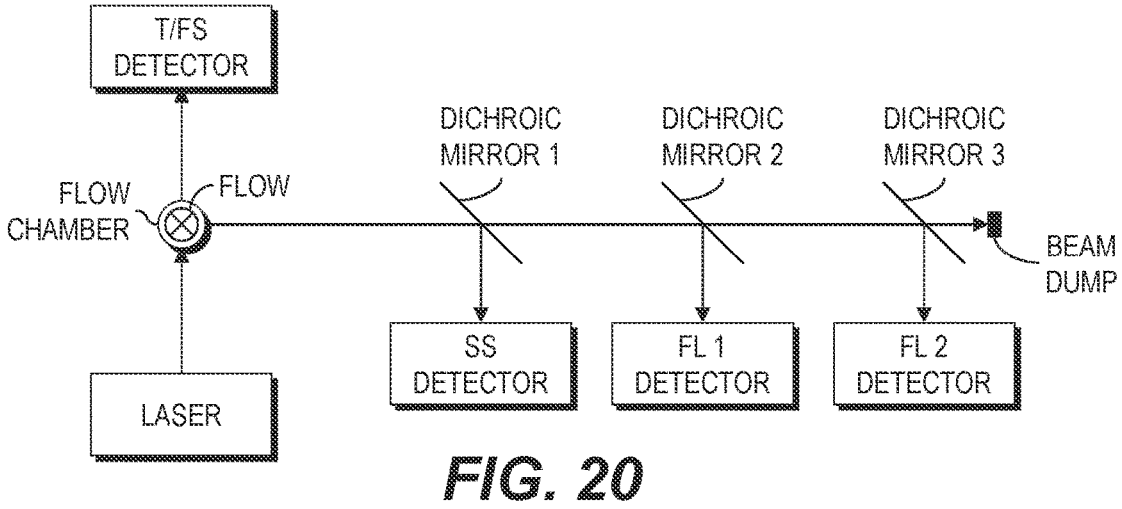
FIG. 20 shows components of an example optical system for multi-channel detection.

FIG. 20 shows an example of a multi-color detection system for flow cytometry. The illustrated system uses dichroic mirrors and filters to separate wavelengths of light. Laser light irradiates a sample flowing in a flow chamber, or a target carried in the sample, e.g., a microparticulate target. A T/FS detector detects transmitted or forward-scattered light. Side-scattered (SS) and fluorescent (FL) light exits the flow chamber to the right in this example. A first dichroic mirror reflects wavelength(s) substantially matching the laser light to a side-scatter detector. A second dichroic mirror reflects wavelength(s) of a first fluorescence of interest to a first fluorescent detector ("FL 1 DETECTOR"). A third dichroic mirror reflects wavelength(s) of a second, different fluorescence of interest to a second fluorescent detector ("FL 2 DETECTOR"). Remaining optical energy can be dissipated by a beam dump.

FIG. 21 is a block diagram of a multi-spectral detector 2100. A light source 2101 is directed to an observation region 2102 when a target can be present for a short period of time while flowing through the flow chamber. The observation region 2102 can be a small region of the flow chamber where the light source 2101, a light-scatter detector 2103, and luminescence collector 2105 can be located. The target can luminesce (e.g., fluoresce), and the luminescence signal can be emitted in all directions. Not all of the light from the light source can be absorbed by the target or sample. Some of the incident light can be scattered by the target as the target flows through the observation region 2102. A light-scatter detector 2103 can collect a portion of the scattered light, generate a signal, and transmit the signal to a multi-channel collection system 2104 that is coupled to the scatter detector 2103 and multi-channel photodetector array 2108. A light collector 2105 such as a lens can be connected to an optical cable which can be connected to a housing 2106. The housing 2106 can contain a light-dispersion element 2107 or other optical disperser, e.g., a spectro unit such as a toroidal reflective grating (e.g., a concave toroidal grating) as described herein. The light-dispersion element 2107 can be in proximity to a photodetector array 2108 that has multiple photodetectors.

Optical fibers (not shown) can be used to convey dispersed light of various wavelengths to the respective photodetectors. For example, a flow cytometer can include multiple optical fibers configured to receive respective light beams from the light-dispersion element 2107 and convey light of the respective light beams to the respective photodetectors of the photodetector array 2108. The proximity of the dispersion element 2107 to the photodetector array 2108 can be adjusted so that the spectrum is projected onto the array (or fiber array; see FIG. 28) to allow each photodetector 2109 in the photodetector array 2108 to receive a portion of the spectrum. Each photodetector in the photodetector array is connected in parallel to the multi-channel collection system 2104. The multi-channel collection system 2104 can contain a high-speed digital signal processor ("DSP") for processing, comparing, or analyzing signals. The multi-channel data collection system 2104 is connected to a processor 2110 for further processing of signals and data storage. The processor 2110 can be located in a computer. The processor 2110 can be a microprocessor, a microcomputer, or even a computer. Processor 2110 can represent processor 1186 or systems 1101 or 1102, FIG. 11.

When a target 2102 is excited by the light source 2101, the target 2102 can luminesce. The target can be in an observation region 2102 where the light source 2101 is directed. The observation region 2102 can be that portion of a flow cytometry chamber accessible to the light collector 2105, the light source 2101, and the detector 2103.

The light source 2101 can be any known light-source suitable for excitation of the target material. For example, the light source 2101 can be a laser or a light emitting diode ("LED") that excites the targeted material to luminesce or fluoresce. The laser can have a multiple number of excitation wavelengths or a single wavelength. The laser can be any gas laser, solid-state laser, semiconductor diode laser, or dye laser. The light source can include a combination of semiconductor diode lasers of any wavelength with each diode having a different wavelength. A band-pass filter 2114 can be placed in front of the laser. If the laser produces more than one line, the unwanted line can be filtered out before it reaches the sample.

The target 2102 can be a biological particle. The biological particle can be stained by a dye that adheres or bonds to the particle. The biological particles can be blood cells, human or animal tissue, infectious agents, bacteria, viruses, yeast, protozoa, or other biological matter. The biological particle can also include a carrier. The carrier can be a small bead which has a surface to which the biological material attaches. The biological particle can also contain a porous carrier bead, which contains biological material inside the pores of the bead. The biological particles can be agents used in biological warfare. The detection of such biological particles can be rapid so that a response by health and public officials can be effected to isolate and quarantine the infected regions.

In flow cytometry, the biological particles can be confined to the center of a flowing stream of fluid through hydrodynamic focusing using a sheath fluid. The biological particles can also flow in a stream of fluid without the sheath. The carrier fluid can transport biological particles through the observation region 2102, allowing the collection of luminescence.

In some examples, a flow cytometer can include an irradiation optical system, e.g., laser 2101, configured to irradiate the sample, e.g., a sample including microparticulate target(s) or to be tested for presence or absence of microparticulate target(s), with incident light configured as an irradiation spot, e.g., a laser spot. The irradiation optical system can additionally or alternatively be configured to irradiate at least one microparticulate target. The flow cytometer can further include a spot-traversal system (e.g., FIGS. 4-7, 11, 12, 15, 19) for causing relative motion of an irradiation spot substantially across the sample in the sensing region. In the example of FIG. 21, the spot-traversal system can include an EOD, an AOD, a rotating reflective polygon, a galvo, or another scanner configured to translate the location of irradiation left and right in the plane of the figure, e.g., to raster-scan the microparticulate sample, e.g., a microparticulate target in the sample, as the sample or the target is carried into or out of the plane of the figure by the flow.

In some examples, a measurement system includes a spot-traversal system such as that described in the previous paragraph for causing relative motion of a sample, or a target therein, and an irradiation spot. The irradiation spot can be or include a focused laser spot having a full-width at half maximum (FWHM) diameter smaller than 2 μm. The sample can include one or more fluorescent markers having respective fluorescence wavelengths. The fluorescent markers can include at least one of: fluorescent-dyed anti-bodies configured to conjugate with molecules of interest (targets) in the sample; or fluorescent tags configured to conjugate with the molecules of interest (targets).

The measurement system can include a flow cytometer, a grating cytometer (e.g., FIG. 5), or another measurement system. For example, the measurement system can include a reflective phase grating over which the sample is arranged. The measurement system can additionally or alternatively include a cover spaced apart from the reflective phase grating, e.g., as discussed herein with reference to FIG. 5, 6, 15, or 16. In some examples, the measurement system can include at least one of a sample inlet and a vacuum port, e.g., as discussed herein with reference to FIG. 3. The vacuum port and the sample inlet can be arranged on opposite sides of a measurement area including the reflective phase grating, also as shown in FIG. 3.

The measurement system can include a gating system configured to provide a gating signal based at least in part on resultant light substantially at a wavelength of the irradiation spot. Examples of gating systems, e.g., based on reflected or refracted laser light, are discussed herein, e.g., with reference to FIG. 4-7 or 11-14. For example, the gating system can determine, based on the resultant light, a tracking signal comprising at least one of a high-frequency (HF) tracking signal or a tangential push-pull (T-PP) signal. The gating system can then provide the gating signal based at least in part on the tracking signal, e.g., as discussed herein with reference to FIGS. 12 and 13.

An optical detection system, e.g., 2106 or FIG. 4-6, 10-12, or 19-21, can detect fluorescent light from at least some of the fluorescent markers irradiated by the irradiation spot. The optical detection system can provide detection signal(s) representing the fluorescent light detected concurrently with a gate-open condition of the gating signal, e.g., as discussed herein with reference to FIG. 13.

In some examples, the optical detection system can detect respective fluorescent light at each of a plurality of wavelengths and provide respective signals of the detection signal(s). For example, the detection signal(s) can include one signal per dye applied to the sample. The measurement system can include a spectral discriminator (e.g., 2107) arranged optically between the sample and the optical detection system. The spectral discriminator can receive the fluorescent light from the sample, e.g., from fluorescing targets or dyes in the sample, and provide the respective fluorescent light at each of the plurality of wavelengths to the optical detection system. The spectral discriminator can include at least one of a dichroic mirror, a grating, a prism, a filter, a polychromator, or a concave toroidal grating.

In some examples, the optical detection system is configured to detect single photon pulses without averaging. For example, the optical detection system can include a Geiger-mode photon counter as described herein.

In some examples, the measurement system can include a flow system configured to move the sample through a flow channel in a direction different from a direction of the relative motion of the sample (or microparticulate target therein) and the irradiation spot. For example, the measurement system can include or be operably connected with a flow cytometer.

Some examples herein include a flow cytometer (FIGS. 19-21) for observing a microparticulate target. The flow cytometer can include a flow chamber including a flow channel formed therein to permit the microparticulate target to flow in a flow direction (e.g., into the plane of FIG. 20 as depicted) through a sensing region of the flow channel. For example, the microparticulate target can be carried in a fluidic sample. The sensing region can include a volume within the flow channel, or a portion of the volume of the flow channel, arranged so that microparticulate targets therein can be irradiated with incident light.

An irradiation optical system (e.g., the laser, or light source 2101) can be configured to irradiate the microparticulate target in the sensing region with incident light. An optical disperser (e.g., a spectro unit, or a dispersion element 2107) can be configured to spectrally disperse at least a first portion of resultant light originating from within the sensing region to provide multiple light beams associated with respective, different wavelengths. As used herein, the term "beam" permits, but does not require, that beams be collimated, or be any particular shape. A "beam" is a generally directional flow of photons, e.g., in a cone angle of <30° or <15°. A beams can include a substantially continuous flow of photons. Additionally or alternatively, a beam can include occasional photons traveling within the beam cone from a common origin region, e.g., the sensing region. For example, a beam can include or consist of one photon per second, or <10 photons/s, or <100 photons/s. Statements that beams can be associated with different wavelengths does not require complete spectral separation between the beams. For example, respective beams may have Gaussian profiles in the spectral domain, and may overlap beyond ±2σ or ±3σ. "Beams" can also be predetermined ranges of a continuous spectral distribution. For example, a continuous spectral distribution can be sampled at specific points, e.g., fiber openings as described herein. The light striking each fiber opening can be considered an individual "beam."

The flow cytometer can include multiple photodetectors, e.g., discrete photodetectors, or photodetectors integrated on a die or in a package. Examples are discussed herein, e.g., with reference to FIGS. 5, 6, 10-13, 19-21, and 28. The photodetectors can be configured to receive respective light beams of the multiple light beams and provide respective resultant-light signals. In some examples, each of the photodetectors comprises a photon detector configured to provide a pulse of the respective resultant-light signal in response to a photon of the respective light beam, e.g., as discussed herein with reference to FIG. 25. In some examples, each of the photodetectors can include a photosensitive integrated-circuit component, e.g., an Si PM or APD, and a drive circuit configured to operate the component in a Geiger mode of operation (e.g., a high-voltage supply).

FIG. 22 is a flowchart of a process 2200 for detecting spectral signatures in flow cytometry. In some examples, devices described herein with reference to FIG. 21 or 28 can be used in carrying out process 2200. In some examples, process 2200 for detecting a biological particle (or other target, and likewise throughout the discussion of FIG. 22) can include flowing 2202 a biological particle through a flow cytometry flow channel or in a groove or on a land, e.g., as described herein. The flow cytometry channel can have an irradiation or detection region for irradiating biological particles or micro-particles. A biological micro-particle can be about 60 μm or less in size. The detection region can be irradiated 2204 with light from a light source, e.g., a laser or other source described herein with reference to FIG. 4-6 or 11. The light source can be a diode laser or an LED. The light can be scattered by a biological particle flowing through the channel (groove, land). The scattered light can be detected by a scattered-light detector that will provide a triggering signal, e.g., photodetectors shown in FIG. 4 or an FS or SS detector such as shown in FIG. 20.

The biological particle can luminesce when it is excited by the light source. The light can be collected by a lens and focused to an optical fiber and transmitted to a slit where the light enters a housing and is dispersed 2206 with a light-dispersion element. The light-dispersion element can disperse the luminescence and project a particular band of light to a photodetector in a photodetector array. The photodetector array will have multiple photodetectors in the array, each photodetector in the array can receive 2208 a particular band of light from the luminescence. Examples are discussed herein, e.g., with reference to FIG. 19.

Each photodiode in the multi-channel photodiode array will transmit an electrical signal when it detects the particular band of light. The signal can be received at a multi-channel collection system, e.g., as in FIG. 19. The multi-channel collection system can form 2210 the signals received from the photodetectors into a combined signal that reveals a spectral signature. The multi-channel collection system can be configured to receive, digitize, and process the signal, thus forming 2210 the spectral signature. The multi-channel collection system can include an integrate-and-hold circuit, an analog MUX, an A/D converter, and a DSP, in some examples. The multi-channel collection system can receive a triggering signal from a light-scatter detector. When the triggering signal is received by the system, the signals from the photodetector array will be received and processed at the integrate and hold circuit. The developed signals will be further processed in the system that forms 2210 the spectral signature. Once the spectral signature is formed it can be transmitted to a processor 1186, which can further process the spectral signature.

Processor 1186 can receive the spectral signatures from the multi-channel collection system. The spectral signatures can be analyzed, and compared 2212 with known signatures.

Known computer algorithms for pattern matching can be used to match the spectral signature. The process of analysis and matching can be run off-line or during the data collection. Since the multi-channel collection system can be triggered about every 10 µsec or even faster, the pattern-matching algorithm operates rapidly, e.g., within the environment of a real-time operating system.

Spectral data sets or spectral signatures can be collected by screening biological particles (or other targets) tagged with, e.g., various organic or inorganic stains, or nanocrystals. The spectral signatures can be subsequently classified into categories using multivariate statistical analysis. A number of multivariate statistical methods can be used ranging from linear decomposition (i.e. Principal Components Analysis, Correspondence Analysis, Karhunen-Loeve transformation) through Independent Component Analysis to nonlinear transformations (e.g., neural networks). In some examples, the processor can use Principal Component Analysis to separate and classify micro-particles. However, the method of choice can depend on the particular application of the spectral screening technology.

The processor can compare 2212 the spectral signature upon reception to a set of known spectral signatures to identify the biological particle. The set of known spectral signatures can be stored in a memory. The processor can compare the spectral signatures upon receipt, or can wait and do the comparison 2212 in a subsequent analysis.

The comparing 2212 can include spectral data sets or spectral signatures collected by screening biological particles tagged with various organic or inorganic stains, or nanocrystals. The spectral signatures can be subsequently classified into categories using multivariate statistical analysis. A number of multivariate statistical methods can be used ranging from linear decomposition through Independent Component Analysis to nonlinear transformations.

The comparing 2212 can be done at data rates where 1000 events per second occur. This corresponds to at least 1000 events where biological particles scatter light and a full analysis of the spectral signature is collected and compared to known biological particles. Further, the comparison can operate at data rates capable of 10,000 events per second. The high speed capability can allow the multi-channel detection system to receive spectral data at about 10,000 events per second.

In some examples, a flow cytometer as discussed herein, e.g., with reference to FIG. 21, can include a memory (e.g., data storage system 1140) storing a plurality of spectral signatures and associated identities and a processor 1186 or 2110 communicatively connected to the memory. The processor can determine a spectral signature of the microparticulate target based at least in part on the respective resultant-light signals (block 2210). The processor can match the spectral signature of the microparticulate target against the plurality of spectral signatures to determine an identity of the microparticulate target (block 2212).

Figure 23:
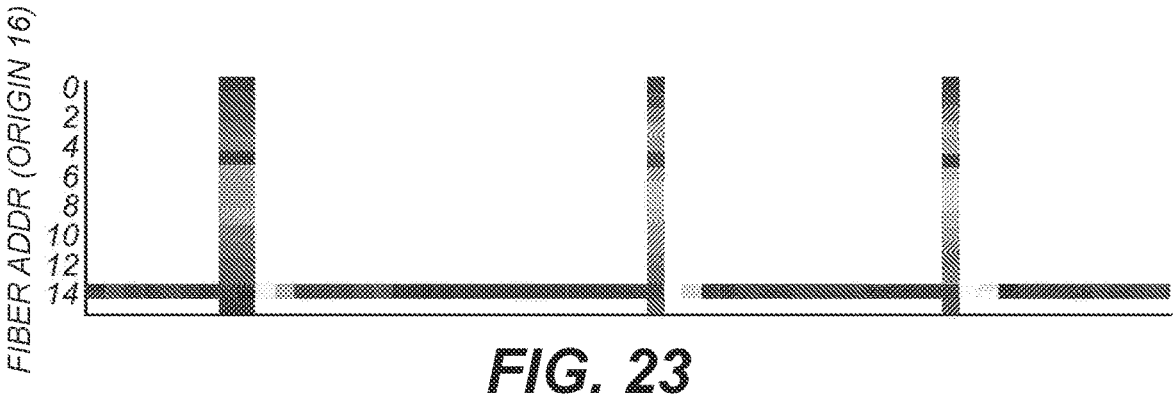
FIG. 23 is a graphical representation of measured data of a fluorescence bead signal from an FC500 flow cytometer and shows relative intensity of light received via various optical fibers.

FIG. 23 shows a graphical representation of experimental measurements of fluorescent beads in an FC500 flow cytometer. Denser hatching (darker) corresponds to a lower signal. White areas represent times and channels for which a significant signal was not detected. Data represented in FIG. 23 and in FIGS. 24 and 25 was captured using a 42-channel (340 nm-800 nm) measurement unit having a spectral resolution of 10.8 nm/channel with equal bandwidth per channel.

Figure 24:
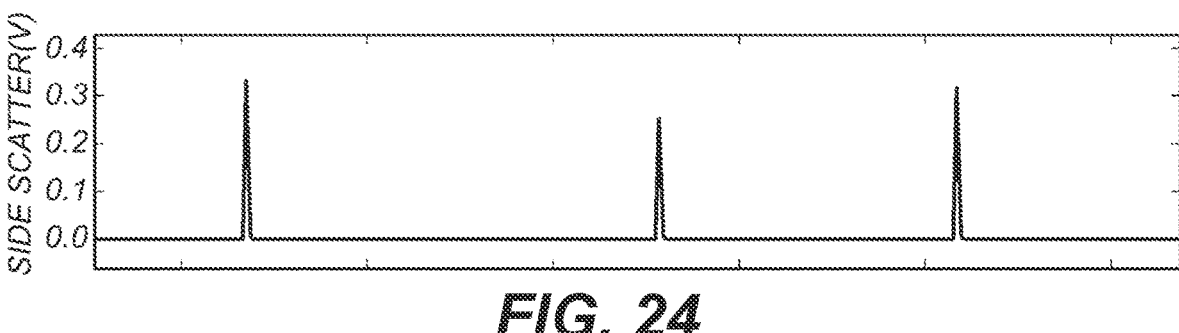
FIG. 24 is a graphical representation of measured data of a fluorescence bead signal from an FC500 and shows an example side scatter signal.

FIG. 24 shows a graphical representation of experimental measurements of a side-scatter signal associated with the measurements depicted in FIG. 23. As shown, the side-scatter measurements are temporally associated with fluorescence measurements. In some examples, fluorescence measurements are triggered based on side-scatter measurements.

Figure 25:
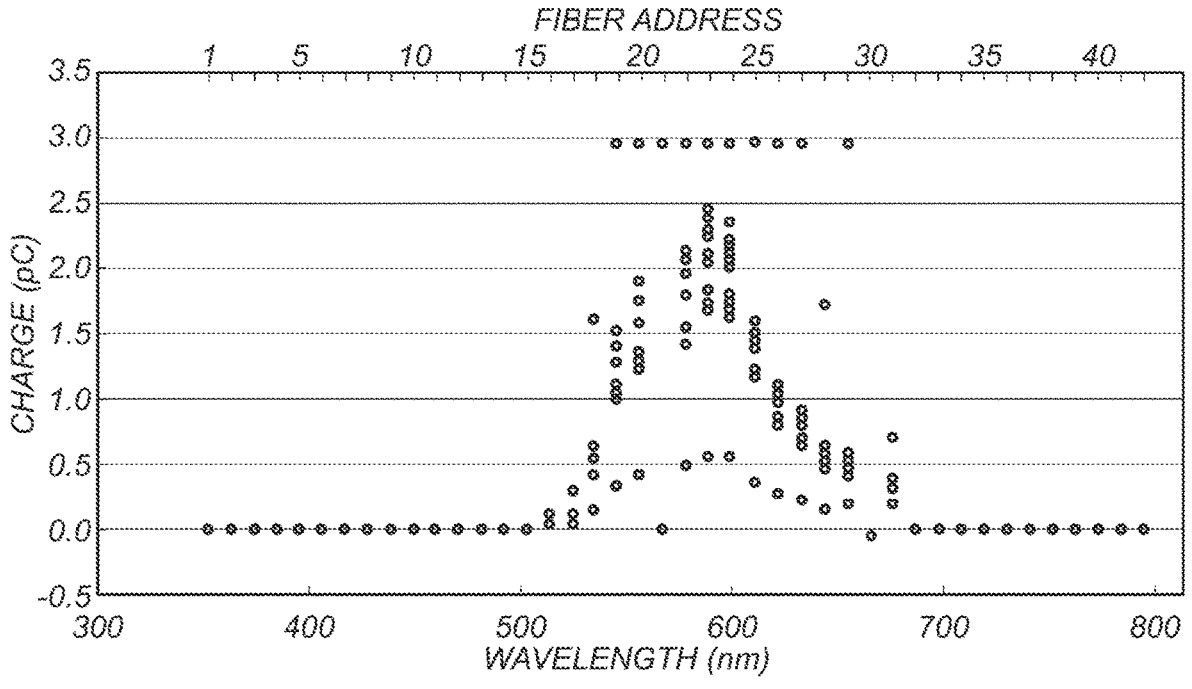
FIG. 25 is a graphical representation of measured data of a fluorescence bead signal from an FC500 and shows charge accumulated on photodetectors associated with various optical fibers.

FIG. 25 shows experimental data of photodetector charge during fluorescence measurements as a function of wavelength (or, equivalently, fiber address). In some examples, one 405 nm photon/sec is an energy of 3.06 eV per second=0.489 E-18 W≈0.5 aW; one 633 nm photon/sec=1.95 eV/sec=0.313 E-18 W≈0.3 aW; and one 780 nm photon/sec=1.59 eV/sec=0.254 E-18 W≈0.25 aW.

Some examples of a tested configuration used, as a photon detector, a microphotomultiplier tube (microPMT) fabricated in an Si MEMS Process. The term "tube," as used herein with reference to microPMTs and other PMTs, does not require a particular shape of PMT. The photocathode was approximately 3 mm×1 mm. The accurate Si process fabrication permitted the microPMT to provide high speed, e.g., a photon pulse width of 4-5 ns and a low dark count, e.g., below 100 counts/sec, and as low as 0.01 counts/sec for voltages above about 100 mV (using a high-voltage supply of −950 V). Another tested configuration used, as a photon detector, a Geiger-mode Si photomultiplier. The photon pulse width was ~600 ps-~900 ps. In some examples, a photon detector can be used that has an internal gain>10000, a photon pulse width<10 ns, and a dark count<1000/s, i.e., <1 count/ms. In some examples, multiple microPMTs or Geiger-mode photomultipliers can be provided on a single integrated-circuit (IC) die, or in a single IC package. For example, 42 channels can be provided in a single package. In some examples, PMTs or APDs operated in Geiger mode (very high voltage; reset required between detections) can be used.

Some examples permit detecting counts between 1 and 1E6 counts per second, which is below the range of conventional fluorescence detectors in flow cytometers.

Figure 26:
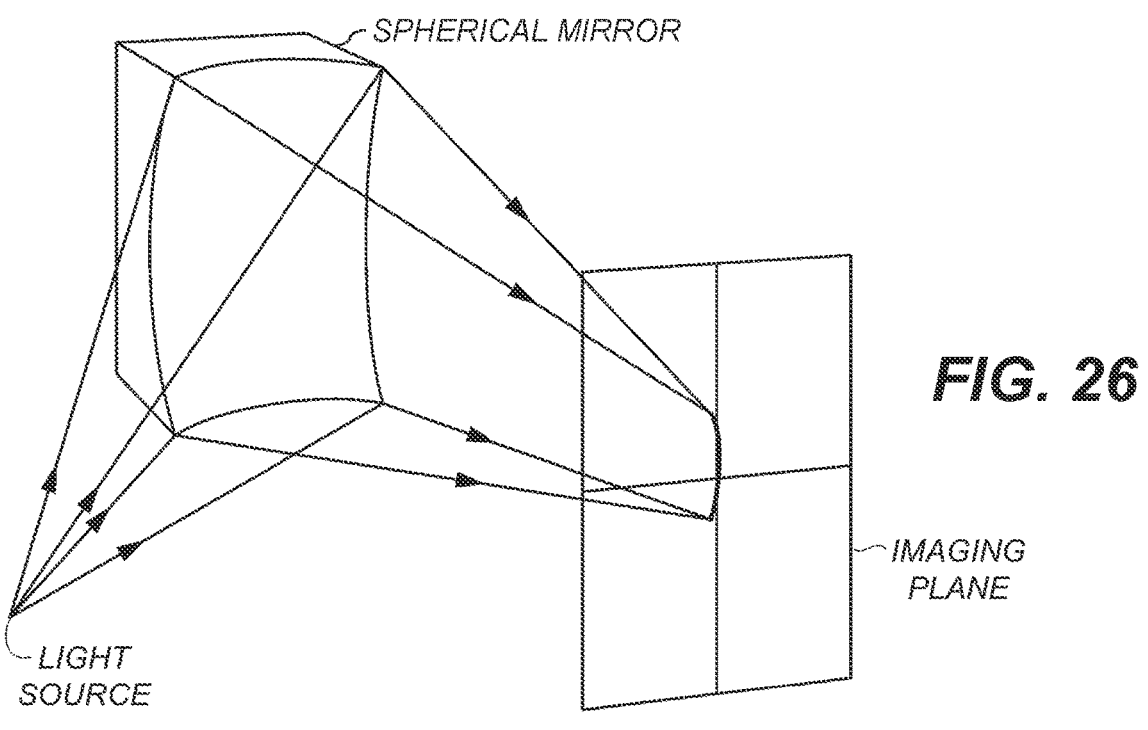
FIG. 26 is a diagram of imaging using a spherical mirror.

FIG. 26 shows an example of optical detection using spherical mirrors. As shown, light from a point source may be spread or smeared along one axis in an imaging plane.

Figure 27:
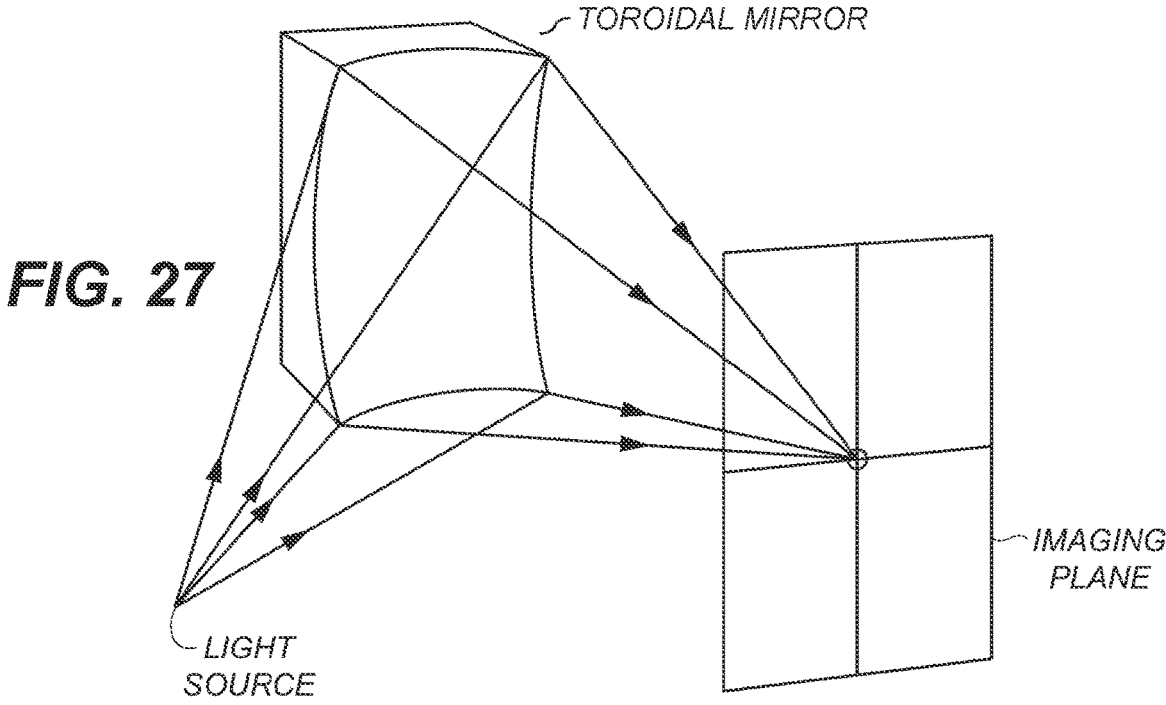
FIG. 27 is a diagram of imaging using a toroidal mirror.

FIG. 27 shows an example of optical detection using toroidal mirrors. As shown, in this example, light from a point source can be focused to a point in an imaging plane. Using toroidal mirrors, as in various examples herein, can therefore provide higher resolution and reduced crosstalk. Using a toroidal mirror grating can reduce aberration when imaging a spot to a fiber array. Using a toroidal mirror grating can permit imaging over a wide wavelength with equal resolution per channel. Using a toroidal mirror grating can provide improved efficiency by reducing the number of reflective elements in the optical path. For example, the toroidal mirror grating can be the only reflective element in the optical path.

In some examples, hyperspectral detection in flow cytometry is a powerful tool for multi-color (e.g., >10 color) phenotypic analysis without compensation. Some prior flow cytometers measure only four colors. Some examples detect and analyze fluorescence signals from a variety of flow cytometers. A tested prototype was used to measure data over a wide wavelength range (340 nm-800 nm) with 42 channels and 16 bit ADC resolution.

In some flow cytometers, fluorescence and side scatter light from the flow cell is collected by a high NA objective lens and collimated to detection optics including dichroic mirrors, bandpass filters, and PMTs. Capturing the collimated fluorescence light with an achromatic lens and optical fiber permits analyzing, e.g., the entire visible light spectrum using a polychromator. A custom polychromator was developed using an aberration corrected Toroidal Mirror Grating and a 42-channel linear fiber array, e.g., as discussed herein with reference to FIG. 27. Example advantages of a tested toroidal mirror grating include wide wavelength coverage from UV 340 nm to IR 800 nm, high spectral resolution with equal bandwidth per channel, high coupling efficiency using just one reflected flat field. The focused spectral line image is coupled into to a 42CH fused silica fiber array with 0.5 mm core diameter and NA=0.22. Once fluorescence light is distributed to the fiber, the signal can be detected by variety of sensors like APD, PMT, or SiPM (Geiger mode APD Array). In some examples, e.g., usable with conventional flow cytometers, 1 mm φ APDs are applied. The amplified photocurrent from the APD is convened to digital signal by a 16-bit current-mode ADC. A tested system was coupled to a conventional FC500 flow cytometer. Fluorescence signals from Rainbow beads were detected, e.g., as discussed herein with reference to FIGS. 23-25. In combination with μPMT by Si-MEMS structure, the sensitivity was sufficient to apply flow analysis in the nanosecond domain. Due to smaller photocathode and dynode area, μPMT and low noise preamplifier with 70 MHz bandwidth, the measured dark counts were less than 10 (~aW level) at room temperature. This permits the analysis of the photon energy spectrum in nanoseconds, referred to herein without limitation as "Photon Spectroscopy" flow cytometry. Various examples permit detailed, high-speed analysis of live cells.

Some examples include a hyperspectral detection system with toroidal mirror grating, 42CH fiber array and advanced electronics. Some examples permit measuring a spectrum range of UV (340 nm) to IR (800 nm) with 10 nm resolution. Some example detection systems can be used with conventional flow systems and flow-cytometry illumination systems. Some examples, e.g., using Si-based photomultipliers and very high speed electronics, permit analysis of each photon's energy level.

Microparticle detection is very useful for intercellular analysis and clinical diagnostics. Various prior schemes do not evaluate smaller than 100 nm particles accurately. There are several way to analyze microparticles, including electron microscopes, Brownian motion analysis, and attempts at using flow cytometry based on Mie scattering. Various examples herein provide Optical Phase Detection ("OPD") using a scanning laser beam (e.g., a very small beam such as a beam having a diameter smaller than the diameter of the particles) to measure liquid phase nanoparticles. Phase detection is based on optical storage principles since optical drives can respond to dimensions on the order of several tens of nanometers. Various examples permit point-of-care monitoring because of the low cost of optical-disc-based mass production.

A tested example was constructed based on the Blu-ray Disc platform to provide high spatial resolution and phase sensitivity. Wavelength 405 nm and NA0.85 optics can provide 250 nm (FWHM) or 390 nm (1/ e²) spot size on the focus plane with 0.35 mW of power. A custom-molded substrate had Al coated land and groove structure with depth λ/8n (40 nm) and pitch 500 nm for matching particle size. Preliminary experiments were performed with dried particle droplets covered with 0.1 mm thickness film. Gold and polymer particles were tested. Gold 100 nm particles showed clear pulse signals with 30% modulation amplitude, and particles as small as 30 nm were also detectable. Some examples can measure at a 10 nm resolution, based on S/N limit data. In a tested configuration, a laser beam illuminated individual particles at appropriate concentration.

Various examples permit evaluating particles or other targets in a liquid environment. This can involve measuring a three dimensional distribution of targets within a sample. Various examples use a 2 μm-gap microchannel formed on a phase grating surface and sealed by 100 μm cover glass with a 500 μm diameter sample inlet made in 1.1 mm polymer supporting substrate. An example was tested, and it was confirmed that the sample liquid filled the micron-gap well by capillary action, thus confirming a functional channel design. Gold 100 nm particle in water showed similar modulation amplitude, and spatial resolution was confirmed for k-dominant particles like gold. In various examples, the magnitude of signal is positively correlated with the refractive index difference (Δn) between transparent biological particles and the medium.

Some examples of OPD permit evaluation of microparticles. A tested configuration using a 2 μm gap microchannel with a 100 μm cover demonstrated measurement of pulse waveforms for gold 100 nm particle. Some examples provide a next generation low cost measurement platform for microparticles in the clinical environment.

Figure 28:
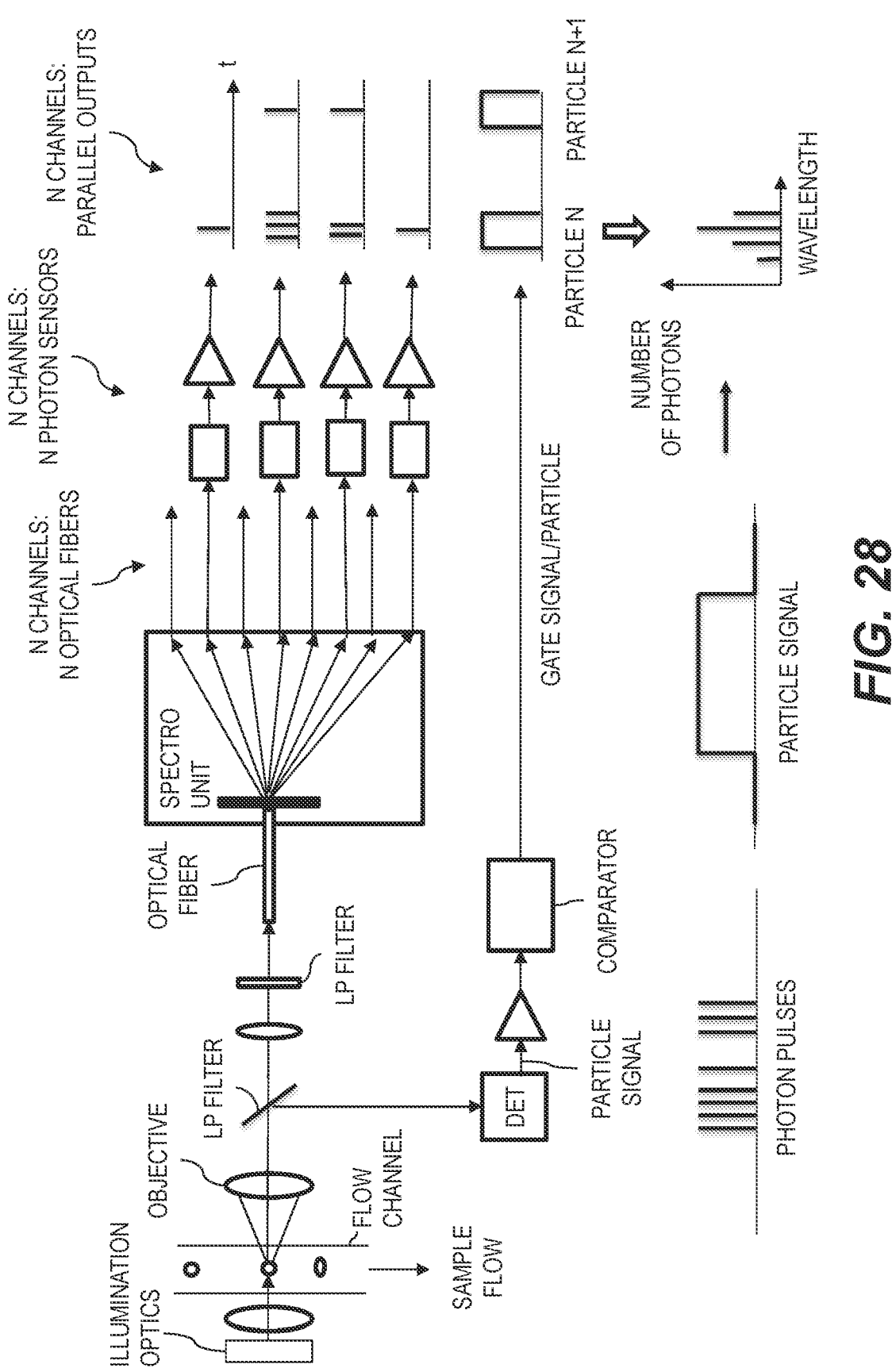
FIG. 28 is a block diagram of an example photon-spectrum detection system for microparticles and shows example signals measured or produced by the example system.

FIG. 28 shows an example photon-spectrum detection system for microparticles or other targets. The illustrated illumination optics can include laser-scanning optics or other optical components, e.g., described herein with reference to FIG. 4-7, 11, 12, or 15. The illustrated spectro unit can include, e.g., a grating, Prism, Dichroic element, or other element described herein with reference to FIG. 19. "DET" is an optical detector or optoelectronic converter, e.g., an APD, photomultiplier, or other device described herein. The illustrated configuration provides parallel detection of N channels using N optical fibers out of the spectro unit and N optical detectors. Each set of outputs from the detectors is gated by a gating signal determined, e.g., based on the side-scatter signal or other gating as discussed herein with reference to FIGS. 11-13. The outputs can be used to determine a histogram of number of photons per wavelength bin (or per photon energy bin).

Some examples provide microparticle fluorescence detection for microparticles in a flow channel. Compared to prior schemes, examples herein permit detecting the limited number of photon emitted by a microparticle due to the small diameter of the microparticle. For example, a 0.1 μm-diameter microparticle might produce ~100 photons, vs. 1,000, 000 photons for a 10 μm diameter particle such as those detected by prior schemes. Prior schemes average over a time period of μs, so cannot detect ns-scale photon pulses.

Various examples provide individual-photon wavelength (energy) detection and analysis. Various examples permit direct photon pulse detection with ns-level time scales using a sensor having very low dark counts. Various examples permit detection of optical signals provided by a multi-channel spectrum unit (rating, prism, dichroic, etc.). Various examples use a gating pulse for each particle to further reduce noise. Various examples determine a particle spectrum quantized in wavelength by the wavelength of each channel, e.g., 10.8 nm/channel×42 channels. Various examples determine a representative spectrum of a sample or a target therein, e.g., as a histogram of captured measurements from the channels over time, e.g., as multiple targets in the sample pass through a flow cytometer.

Some examples use a toroidal or other concave mirror grating such as those used in polychromators. The grooves of the grating can be etched into a curved surface or formed optically in a holographic grating, e.g., formed from a photoresists, that has a concave surface. Light is directed onto the grating surface from an input fiber. The light can be focused, conveyed in a waveguide such as an optical fiber, or otherwise caused to illuminate at least a portion of the grating surface. The grating disperses the reflected light spectrally, so reflection angle depends on wavelength. Some concave gratings both disperse wavelengths of light and focus the dispersed light onto an imaging plane.

In some examples herein, the grating is designed to disperse the reflected light evenly along a line. Along the line is positioned a linear fiber array, e.g., of 500 μm-core-diameter fibers on a 570 μm pitch. The distance between the grating and the array can be determined to provide a desired spectral bandwidth per fiber, e.g., 10.8 nm per fiber. Using toroidal gratings can reduce spectral aberration compared to other gratings. Plane gratings can additionally or alternatively be used, e.g., in conjunction with imaging optics to focus the spectrally-dispersed output light onto a fiber array or other device in an imaging plane of the imaging optics.

In some examples, a flow cytometer, e.g., as discussed herein with reference to FIG. 21, can include a memory (e.g., 1140). A photosensor as discussed above can receive at least a second portion of the resultant light and provide a pre-gating signal representing the second portion of the resultant light. For example, the photosensor can include a photodiode or split photodiode as discussed herein with reference to FIG. 4-7, 12, or 28 to provide an HF, T-PP, or R-PP signal as the pre-gating signal. A gating circuit can determine measurement time period(s) based on the pre-gating signal. Examples are discussed herein, e.g., with reference to FIGS. 10-14. Processor 1186 can store into the memory, only during the measurement time period(s), data representing the resultant-light signals. For example, each resultant-light signal can be associated with a time or times, such as shown on the X-axis in FIG. 13. For example, individual resultant-light signals can be sampled at discrete time intervals and each sample can be associated with a respective timestamp. In some examples, resultant-light signal(s) (e.g., samples thereof) associated with times within the measurement time period(s) can be stored into the memory. In some examples, resultant-light signals (e.g., samples thereof) associated with times outside the measurement time period(s) are not stored into the memory. Examples are discussed herein, e.g., with reference to FIGS. 12 and 28.

FIG. 29 is a flowchart of a process 2900 for measuring a sample or target(s) thereon, or determining whether a microparticulate sample contains a particular target. Process 2900 can be carried out, e.g., by devices such as discussed herein with reference to FIG. 1-21 or 26-28, e.g., processor 1186 and related components. Blocks 2902 can be preceded by blocks 1405 or 1410, FIG. 14. Blocks 2906 and 2908 can be performed before, after, or concurrently with blocks 2910 and 2912.

In some examples, at block 2902 ("apply sample"), a sample can be disposed over a reflective phase grating at least partly in a sensing region of the reflective phase grating. Additionally or alternatively, block 2902 can include receiving a sample at the reflective phase grating at least partly in the sensing region. The sensing region can include, e.g., a flow channel over a disc-on-chip. Block 2902 can be carried out by the sample delivery system shown in FIG. 11. For example, block 2902 can include positioning at least a portion of a fluidic sample in contact with at least a portion of the reflective phase grating or an LOC including the reflective phase grating. The reflective phase grating or other structures of the LOC can then draw the fluidic sample over the reflective phase grating by capillary action. Examples are discussed herein, e.g., with reference to FIG. 18. The sample can include at least one microparticulate target, in some examples.

In some examples, at block 2904, after block 2902, at least a portion of the sensing region can be irradiated. This can be done, e.g., with focused laser or LED light.

In some examples, at block 2906, at least some resultant light from the sensing region can be dispersed to provide respective light beams. Examples are discussed herein, e.g., with reference to FIG. 21. Each of the light beams can be associated with a respective wavelength range. The respective wavelength ranges can be disjoint or partly overlapping, in some examples.

In some examples, at block 2908, at least one detector can be operated to count photons of respective ones of the light beams and to provide respective beam signals. Examples are discussed herein, e.g., with reference to at least FIG. 12, 19, 21, or 23-28. For example, processor 1186 can activate or otherwise operate Geiger-mode or other photon counters. Block 2908 can be followed by block 2910.

In some examples, at block 2910, at least some resultant light from the sensing region can be detected to provide at least one resultant-light signal. The at least some resultant light can overlap with the light discussed with reference to block 2906, or can be different light. For example, in the system of FIG. 5, block 2906 can include dispersing fluorescence light using a spectro unit, and block 2910 can include detecting light at the wavelength of the laser, e.g., 405 nm, to provide the focus and tracking error signals. The light fluxes discussed with reference to blocks 2906 and 2910 can be at a fluorescent wavelength or wavelength(s), or at different wavelengths.

In some examples, at block 2912, a gating signal can be determined based at least in part on the at least one resultant light signal. Examples are discussed herein, e.g., with reference to FIG. 12-14 or 28. For example, the gating signal can include a side-scatter signal, a tracking signal, or a difference of signals. Block 2912 can be followed by block 2906 (connector omitted for brevity).

In some examples, at block 2914, at least one of the beam signals can be gated based at least in part on the gating signal to provide one or more sample-fluorescence signal(s) associated with respective wavelength range(s). For example, beam signals can be suppressed or ignored during a gate-closed condition of the gating signal, or digital values representing the beam signals can be collected or stored only during a gate-open condition of the gating signal.

In some examples, blocks 2916 and 2918 can be performed concurrently with block 2904. Blocks 2916 and 2918 can be performed concurrently with each other, or sequentially.

In some examples, at block 2916, concurrently with the irradiating, relative motion of an irradiation spot and the reflective phase grating can be caused, e.g., by processor 1186 ("move spot w.r.t.," with respect to, "grating"). For example, processor 1186 can operate a motion system to scan an irradiation spot, spin a lab-on-disc, or translate a lab-on-chip, or can operate a flow system to cause a fluidic sample to flow past the irradiation spot. Examples of these techniques are discussed herein. Block 2916 can include moving exactly one of the irradiation spot, the grating, and the sample; or any two of those; or all three of those, in any combination, in some examples.

In some examples, at block 2918, concurrently with the irradiating, the at least one resultant-light signal can be provided comprising a tracking signal. For example, block 2914 can include determining an HF, R-PP, or T-PP signal, and providing the determined signal as the at least one resultant-light signal.

In some examples using blocks 2916 and 2918, block 2912 can include determining the gating signal based at least in part on the tracking signal. This is represented graphically by the dashed line. Examples are discussed herein, e.g., with reference to FIGS. 12-14.

In some examples, process 2900 can include blocks 2902, 2904, 2910, 2912, and 2914. In place of the beam signals, block 2914 can include gating at least one of the resultant light signal(s) based at least in part upon the gating signal to provide one or more fluorescence signal(s) associated with respective wavelength range(s) of the resultant light. In some examples, process 2900 can include counting photons of resultant light in at least one of the wavelength range(s) to provide respective one(s) of the resultant-light signal(s).

EXAMPLE CLAUSES

A: A measurement system, comprising: a spot-traversal system for causing relative motion of a sample and an irradiation spot, wherein the sample includes one or more fluorescent markers having respective fluorescence wavelengths; and an optical detection system configured to detect fluorescent light from at least some of the fluorescent markers irradiated by the irradiation spot.

B: The system according to paragraph A, wherein the fluorescent markers include fluorescent-dyed anti-bodies configured to conjugate with molecules of interest in the sample, or include fluorescent tags configured to conjugate with the molecules of interest.

C: The system according to paragraph A or B, wherein the irradiation spot includes a focused laser spot with a full-width at half maximum diameter smaller than two microns.

D: The system according to any of paragraphs A-C, the optical detection system configured to detect light at each of a plurality of wavelengths and the system further including a spectral discriminator arranged between the sample and the optical system, the spectral discriminator configured to provide light at wavelength(s) of the plurality of wavelengths to the optical detection system.

E: The system according to paragraph D, wherein the spectral discriminator includes at least one of a dichroic mirror, a grating, a prism, a filter, or a polychromator.

F: The system according to any of paragraphs A-E, wherein the optical detection system is configured to detect single photon pulses without averaging.

G: The system according to any of paragraphs A-F, further including a tracking system configured to provide one or more tracking signals based at least in part on resultant light substantially at a wavelength of the irradiation spot, wherein the optical detection system is configured to gate detected photon signals based at least in part on one(s) of the tracking signal(s)

H: The system according to paragraph G, wherein the gating is based at least in part on a high-frequency (HF) tracking signal, a tangential push-pull (T-PP) signal, or both.

I: The system according to any of paragraphs A-H, further comprising a reflective phase grating over which the sample is arranged.

J: The system according to paragraph I, further including a cover spaced apart from the reflective phase grating.

K: The system according to any of paragraphs A-J, further including a sample inlet.

L: The system according to any of paragraphs A-K, further including a vacuum port.

M: The system according to paragraph L, wherein the vacuum port and the sample inlet are arranged on opposite sides of a measurement area including the reflective phase grating.

N: A method of measuring, comprising irradiating a reflective phase grating; measuring resultant light in a selected wavelength range; and gating the measured light based at least in part upon a tracking signal.

O: The method according to paragraph N, further including disposing a sample over the reflective phase grating or receiving a sample at the reflective phase grating.

P: The method according to paragraph N or O, further including causing relative motion of an irradiation spot and the reflective phase grating.

Q: A method of measuring a sample, comprising: disposing the sample over a reflective phase grating or receiving the sample at the reflective phase grating; subsequently, irradiating the reflective phase grating; measuring resultant light to provide resultant-light signal(s); determining a gating signal based at least in part on at least one of the resultant light signal(s); and gating at least one of the resultant light signal(s) based at least in part upon the gating signal to provide one or more fluorescence signal(s) associated with respective wavelength range(s) of the resultant light.

R: The method according to any paragraph Q, further comprising: counting photons of resultant light in at least one of the wavelength range(s) to provide respective one(s) of the resultant-light signal(s).

S: The method according to paragraph R, further comprising: spectrally dispersing at least some of the resultant light to provide respective dispersed light beams, wherein each of the dispersed light beams is associated with a respective one of the wavelength range(s); and operating a plurality of detectors to count the photons of respective ones of the dispersed light beams and to provide respective ones of the resultant-light signals.

T: The method according to any of paragraphs Q-S, further comprising: concurrently with the irradiating: causing relative motion between an irradiation spot and the reflective phase grating, e.g., in a first direction; and measuring the resultant light to provide at least one tracking signal of the resultant-light signal(s); and determining the gating signal based at least in part on the tracking signal.

U: A measurement system, comprising: a spot-traversal system for causing relative motion between a sample and an irradiation spot in a first direction, wherein the sample includes one or more fluorescent markers having respective fluorescence wavelengths; a gating system configured to provide a gating signal based at least in part on resultant light substantially at a wavelength of the irradiation spot; and an optical detection system configured to: detect fluorescent light from at least some of the fluorescent markers irradiated by the irradiation spot; and provide detection signal(s) representing the fluorescent light detected concurrently with a gate-open condition of the gating signal.

V: The measurement system according to paragraph U, wherein: the optical detection system is configured to detect respective fluorescent light at each of a plurality of wavelengths and provide respective signals of the detection signal(s); and the measurement system further comprises a spectral discriminator arranged optically between the sample and the optical detection system, the spectral discriminator configured to receive the fluorescent light from the sample and provide the respective fluorescent light at each of the plurality of wavelengths to the optical detection system.

W: The measurement system according to paragraph V, wherein the spectral discriminator comprises at least one of a dichroic mirror, a grating, a prism, a filter, a polychromator, or a concave toroidal grating.

X: The measurement system according to any of paragraphs U-W, further comprising a flow system configured to move the sample through a flow channel in a second direction different from the first direction.

Y: The measurement system according to any of paragraphs wherein the optical detection system is configured to detect single photon pulses without averaging.

Z: The measurement system according to any of paragraphs U-Y, wherein the fluorescent markers comprise at least one of: fluorescent-dyed anti-bodies configured to conjugate with at least one predetermined type of molecules in the sample; or fluorescent tags configured to conjugate with the at least one predetermined type of molecules.

AA: The measurement system according to any of paragraphs U-Z, wherein the irradiation spot comprises a focused laser spot having a full-width at half maximum (FWHM) diameter smaller than two microns.

AB: The measurement system according to any of paragraphs U-AA, wherein the gating system is configured to: determine, based on the resultant light, a tracking signal comprising at least one of a high-frequency (HF) tracking signal or a tangential push-pull (T-PP) signal; and provide the gating signal based at least in part on the tracking signal.

AC: The measurement system according to any of paragraphs U-AB, further comprising a reflective phase grating over which the sample is arranged.

AD: The measurement system according to paragraph AC, further comprising a cover spaced apart from the reflective phase grating.

AE: The measurement system according to any of paragraphs U-AD, further comprising a sample inlet.

AF: The measurement system according to any of paragraphs U-AE, further comprising a vacuum port.

AG: The measurement system according to paragraph AF, wherein the vacuum port and the sample inlet are arranged on opposite sides of a measurement area including the reflective phase grating.

AH: A flow cytometer for observing a microparticulate target, the flow cytometer comprising: a flow chamber including a flow channel formed therein to permit the microparticulate target to flow in a flow direction through a sensing region of the flow channel; an irradiation optical system configured to irradiate the microparticulate target in the sensing region with incident light; an optical disperser configured to spectrally disperse at least a first portion of resultant light originating from within the sensing region to provide multiple light beams associated with respective, different wavelengths; and multiple photodetectors configured to receive respective light beams of the multiple light beams and provide respective resultant-light signals.

AI: The flow cytometer according to paragraph AH, further comprising: a memory; a photosensor configured to receive at least a second portion of the resultant light and provide a pre-gating signal representing the second portion of the resultant light; a gating circuit configured to determine measurement time period(s)

based on the pre-gating signal; and a processor configured to perform at least one of the following: (i) storing into the memory, only during the measurement time period(s), data representing the resultant-light signals; or (ii) storing into the memory data representing signal (s) of the resultant-light signals, the signal(s) associated with period(s) of the measurement time period(s).

AJ: The flow cytometer according to paragraph AH or AI, wherein each of the photodetectors comprises a photon detector configured to provide a pulse of the respective resultant-light signal in response to a photon of the respective light beam.

AK: The flow cytometer according to any of paragraphs AH-AJ, further comprising: a memory storing a plurality of spectral signatures and associated identities; and a processor communicatively connected to the memory and configured to: determine a spectral signature of the microparticulate target based at least in part on the respective resultant-light signals; and match the spectral signature of the microparticulate target against the plurality of spectral signatures to determine an identity of the microparticulate target.

AL: The flow cytometer according to any of paragraphs AH-AK, wherein each of the photodetectors comprises a photosensitive integrated-circuit component and a drive circuit configured to operate the photosensitive integrated-circuit component in a Geiger mode of operation.

AM: The flow cytometer according to any of paragraphs AH-AL, further comprising multiple optical fibers configured to receive the respective light beams and convey light of the respective light beams to the respective photodetectors.

AN: The flow cytometer according to any of paragraphs AH-AM, wherein the optical disperser comprises a concave toroidal grating.

AO: The flow cytometer according to any of paragraphs AH-AN, wherein: the irradiation optical system is configured to irradiate the microparticulate target with the incident light configured as an irradiation spot; and the flow cytometer further comprises a spot-traversal system for causing relative motion of an irradiation spot substantially across the microparticulate target in the sensing region.

AP: The flow cytometer according to any of paragraphs AH-AO, further comprising a flow system configured to cause a fluidic sample to flow through the sensing region, wherein the fluidic sample at least partly carries or comprises the microparticulate target.

AQ: A method of measuring a sample, comprising: disposing a sample over the reflective phase grating at least partly in a sensing region of the reflective phase grating, or receiving a sample at the reflective phase grating at least partly in the sensing region; subsequently, irradiating at least a portion of the sensing region; spectrally dispersing at least some resultant light from the sensing region to provide respective light beams, wherein each of the light beams is associated with a respective wavelength range; operating at least one detector to count photons of respective ones of the light beams and to provide respective beam signals; detecting at least some resultant light from the sensing region to provide at least one resultant-light signal; determining a gating signal based at least in part on the at least one resultant light signal; and gating at least one of the beam signals based at least in part on the gating signal to provide one or more sample-fluorescence signal(s) associated with respective wavelength range (s).

AR: The method according to paragraph AQ, further comprising: concurrently with the irradiating: causing relative motion of an irradiation spot and the reflective phase grating; and providing the at least one resultant-light signal comprising a tracking signal; and determining the gating signal based at least in part on the tracking signal.

AS: A computer-readable medium, e.g., a computer storage medium, having thereon computer-executable instructions, the computer-executable instructions upon execution configuring a computer to perform operations as any of paragraphs N-P recites.

AT: A device comprising: a processor; and a computer-readable medium, e.g., a computer storage medium, having thereon computer-executable instructions, the computer-executable instructions upon execution by the processor configuring the device to perform operations as any of paragraphs N-P recites.

AU: A system comprising: means for processing; and means for storing having thereon computer-executable instructions, the computer-executable instructions including means to configure the system to carry out a method as any of paragraphs N-P recites.

AV: A computer-readable medium, e.g., a computer storage medium, having thereon computer-executable instructions, the computer-executable instructions upon execution configuring a computer to perform operations as any of paragraphs Q-T recites.

AW: A device comprising: a processor; and a computer-readable medium, e.g., a computer storage medium, having thereon computer-executable instructions, the computer-executable instructions upon execution by the processor configuring the device to perform operations as any of paragraphs Q-T recites.

AX: A system comprising: means for processing; and means for storing having thereon computer-executable instructions, the computer-executable instructions including means to configure the system to carry out a method as any of paragraphs Q-T recites.

AY: A computer-readable medium, e.g., a computer storage medium, having thereon computer-executable instructions, the computer-executable instructions upon execution configuring a computer to perform operations as any of paragraphs AQ-AR recites.

AZ: A device comprising: a processor; and a computer-readable medium, e.g., a computer storage medium, having thereon computer-executable instructions, the computer-executable instructions upon execution by the processor configuring the device to perform operations as any of paragraphs AQ-AR recites.

BA: A system comprising: means for processing; and means for storing having thereon computer-executable instructions, the computer-executable instructions including means to configure the system to carry out a method as any of paragraphs AQ-AR recites.

CONCLUSION

Some examples herein provide photon-counting flow cytometry, or photon-counting cytometry on a reflective grating such as a reflective phase grating. Various examples provide parallel or simultaneous detection of multiple colors of fluorescence, e.g., from samples in a flow channel or on a reflective grating. Various examples can use a single color of illumination. Various examples can provide individual measurements associated with many respective particles in a short period of time, e.g., while the particles (or other targets) flow through a flow chamber or are moved past the readout system on a disc-format lab-on-chip. This can permit, e.g., rapidly counting or sorting cells based on whether specific tagged organelles therein are alive or dead. Various examples scan a small irradiation spot across a particle to provide rapid measurement of interior structures of the particle. Various examples permit combining photon counting, to determine intensity of fluorescence and to count microparticles, with time-domain analysis such as that used in Förster Resonance Energy Transfer (FRET) spectroscopy.

The invention is inclusive of combinations of aspects described herein. References to "a particular aspect" (or "embodiment" or "version") and the like refer to features that are present in at least one aspect described herein. Separate references to "an aspect" (or "embodiment") or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

Although the techniques have been described in language specific to structural features and/or methodological acts, it is to be understood that the appended claims are not necessarily limited to the features and/or acts described. Rather, the features and acts are described as example implementations of such techniques. For example, network 1150, processor 1186, and other structures described herein for which multiple types of implementing devices or structures are listed can include any of the listed types, and/or multiples and/or combinations thereof.

The operations of the example processes are illustrated in individual blocks and summarized with reference to those blocks. The processes are illustrated as logical flows of blocks, each block of which can represent one or more operations that can be implemented in hardware, software, and/or a combination thereof. In the context of software, the operations represent computer-executable instructions stored on one or more computer-readable media that, when executed by one or more processors, enable the one or more processors to perform the recited operations. Generally, computer-executable instructions include routines, programs, objects, modules, components, data structures, and the like that perform particular functions and/or implement particular abstract data types. The order in which the operations are described is not intended to be construed as a limitation, and any number of the described operations can be executed in any order, combined in any order, subdivided into multiple sub-operations, and/or executed in parallel to implement the described processes. The described processes can be performed by resources associated with one or more data processing systems 1101 or 1102 or processor(s) 1186 or 2110 such as one or more internal and/or external CPUs and/or GPUs, and/or one or more pieces of hardware logic such as FPGAs, DSPs, and/or other types described above.

All of the methods and processes described above can be embodied in, and fully automated via, software code modules executed by one or more computers and/or processors. The code modules can be embodied in any type of computer-readable medium. Some and/or all of the methods can be embodied in specialized computer hardware.

Conditional language such as, among others, "can," "could," "might" and/or "may," unless specifically stated otherwise, are understood within the context to present that certain examples include, while other examples do not include, certain features, elements and/or steps. Thus, such conditional language is not generally intended to imply that certain features, elements and/or steps are in any way required for one or more examples and/or that one or more examples necessarily include logic for deciding, with and/or without user input and/or prompting, whether certain features, elements and/or steps are included and/or are to be performed in any particular example. The word "or" and the phrase "and/or" are used herein in an inclusive sense unless specifically stated otherwise. Accordingly, conjunctive language such as the phrases "X, Y, or Z," "at least X, Y, or Z," or "at least one of X, Y or Z," unless specifically stated otherwise, is to be understood as signifying that an item, term, etc., can be either X, Y, or Z, or a combination thereof.

Any routine descriptions, elements and/or blocks in the flow diagrams described herein and/or depicted in the attached figures should be understood as potentially representing modules, segments, and/or portions of code that include one or more executable instructions for implementing specific logical functions and/or elements in the routine. Alternative implementations are included within the scope of the examples described herein in which elements and/or functions can be deleted and/or executed out of order from any order shown or discussed, including substantially synchronously and/or in reverse order, depending on the functionality involved as would be understood by those skilled in the art. Examples herein are nonlimiting unless expressly stated otherwise, regardless of whether or not they are explicitly described as being nonlimiting. It should be emphasized that many variations and modifications can be made to the above-described examples, the elements of which are to be understood as being among other acceptable examples. All such modifications and variations are intended to be included herein within the scope of this disclosure and protected by the following claims. Moreover, in the claims, any reference to a group of items provided by a preceding claim clause is a reference to at least some of the items in the group of items, unless specifically stated otherwise.

The invention claimed is:

1. A measurement system, comprising:
a light source adapted to direct light to an irradiation spot;
a spot-traversal system for causing relative motion between a sample and the irradiation spot in a first direction, wherein the relative motion is caused by moving the sample or moving the irradiation spot utilizing one or more of rasterizers, polygons or other movable mirrors, mirror or micromirror arrays, fixed mirrors, rotational, linear, XY, or XYZ stages or drives, lenses, and gratings wherein the sample includes one or more fluorescent markers having respective fluorescence wavelengths, wherein light sourced from the light source incident on the sample generates a resultant light from the sample,
wherein the sample includes particles including blood cells, human or animal tissue, infectious agents, bacteria, viruses, yeast, protozoa, or a combination thereof;
a gating system including a beam splitter adapted to split the resultant light into one or more split beams and further including i) corresponding detectors configured to detect each of the one or more split beams and thereby generate a detector-output signal corresponding therefor, and ii) corresponding comparators configured to receive each of the detector-output signals and compare to a predetermined threshold to thereby generate a comparator-output signal corresponding therefor, and wherein the comparator-output signals are configured to provide a gating signal based at least in part on resultant light substantially at a wavelength of the irradiation spot;
an optical detection system including one or more detectors and one or more comparators and configured to:
i) detect fluorescent light from at least some of the fluorescent markers irradiated by the irradiation spot; and
ii) provide one or more detection signals representing the fluorescent light detected concurrently with a gate-open condition of the gating signal, and
a flow system including a vertical flow channel configured to move the sample through the vertical flow channel in a second direction different from the first direction based on vacuum forces established by at least one vacuum port.

2. The measurement system according to claim 1, wherein:
the optical detection system is configured to detect respective fluorescent light at each of a plurality of wavelengths and provide respective signals of the detection signal(s); and
the measurement system further comprises a spectral discriminator including at least one of a dichroic mirror, a grating, a prism, a filter, a polychromator, or a concave toroidal grating arranged optically between the sample and the optical detection system, the spectral discriminator configured to receive the fluorescent light from the sample and provide the respective fluorescent light at each of the plurality of wavelengths to the optical detection system.

3. The measurement system according to claim 2, wherein the spectral discriminator comprises at least one of a dichroic mirror, a grating, a prism, a filter, a polychromator, or a concave toroidal grating.

4. The measurement system according to claim 1, wherein the optical detection system is configured to detect single photon pulses without averaging.

5. The measurement system according to claim 1, wherein the one or more detection signals generated by the optical detection system is based on fluorescent markers which comprise at least one of:
fluorescent-dyed antibodies configured to conjugate with at least one predetermined type of molecules in the sample; or
fluorescent tags configured to conjugate with the at least one predetermined type of molecules.

6. The measurement system according to claim 1, wherein the gating system is configured to:
determine, based on the resultant light, a tracking signal comprising at least one of a high-frequency (HF) tracking signal or a tangential push-pull (T-PP) signal; and
provide the gating signal based at least in part on the tracking signal.

7. The measurement system according to claim 1, further comprising a reflective phase grating constructed as a substrate with dissimilar surface contours including grooves and lands over which the sample is arranged.

8. The measurement system according to claim 7, further comprising a cover spaced apart from the reflective phase grating.

* * * * *